(12) United States Patent  
Schmitt et al.

(10) Patent No.: US 10,597,300 B2  
(45) Date of Patent: Mar. 24, 2020

(54) EMM-28, A NOVEL SYNTHETIC CRYSTALLINE MATERIAL, ITS PREPARATION AND USE

(71) Applicant: ExxonMobil Research and Engineering Company, Annandale, NJ (US)

(72) Inventors: Kirk D. Schmitt, Pennington, NJ (US); Hilda B. Vroman, Piscataway, NJ (US); Allen W. Burton, Stewartsville, NJ (US); Michael A. Marella, Easton, PA (US); Ross Mabon, Whitehall, PA (US); Simon C. Weston, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/278,470

(22) Filed: Feb. 18, 2019

(65) Prior Publication Data  
US 2019/0218106 A1 Jul. 18, 2019

Related U.S. Application Data

(62) Division of application No. 15/359,644, filed on Nov. 23, 2016, now Pat. No. 10,252,918.

(Continued)

(51) Int. Cl.  
*C07D 207/04* (2006.01)  
*C01B 39/48* (2006.01)  
(Continued)

(52) U.S. Cl.  
CPC ............. *C01B 39/48* (2013.01); *B01D 15/36* (2013.01); *B01D 53/02* (2013.01); *B01J 20/18* (2013.01);  
(Continued)

(58) Field of Classification Search  
CPC ............................ C07D 207/04; C07C 303/08  
See application file for complete search history.

(56) References Cited

U.S. PATENT DOCUMENTS

| 7,651,677 B1 | 1/2010 | Strohmaier et al. |
| 10,252,918 B2 * | 4/2019 | Schmitt .................. C01B 39/48 |

(Continued)

FOREIGN PATENT DOCUMENTS

| EP | 0042226 A1 | 2/1981 |
| WO | 2013019462 A1 | 2/2013 |
| WO | 2014100218 A1 | 6/2014 |

OTHER PUBLICATIONS

Unknown, "Group notation revised in periodic table", Chemical & Engineering News, May 27, 1985, pp. 26-27, vol. 63, Iss. 5, American Chemical Society.

(Continued)

*Primary Examiner* — David M Brunsman  
(74) *Attorney, Agent, or Firm* — Andrew T. Ward; Priya G. Prasad

(57) ABSTRACT

A novel synthetic crystalline material, EMM-28, can be synthesized in the presence of an organic structure directing agent (Q) selected from one or more of the following dications:

(Continued)

EMM-28 may be used in organic compound conversion reactions and sorptive processes.

16 Claims, 1 Drawing Sheet

Related U.S. Application Data

(60) Provisional application No. 62/262,950, filed on Dec. 4, 2015.

(51) Int. Cl.

| | | |
|---|---|---|
| *B01J 20/18* | (2006.01) | |
| *B01J 20/30* | (2006.01) | |
| *B01J 29/70* | (2006.01) | |
| *B01J 37/04* | (2006.01) | |
| *B01J 37/10* | (2006.01) | |
| *B01J 37/00* | (2006.01) | |
| *C07C 303/08* | (2006.01) | |
| *B01D 15/36* | (2006.01) | |
| *B01D 53/02* | (2006.01) | |
| *B01J 29/035* | (2006.01) | |

(52) U.S. Cl.
CPC ........... *B01J 20/3085* (2013.01); *B01J 29/70* (2013.01); *B01J 37/0018* (2013.01); *B01J 37/04* (2013.01); *B01J 37/10* (2013.01); *C07C 303/08* (2013.01); *C07D 207/04* (2013.01); *B01D 2253/108* (2013.01); *B01D 2253/1085* (2013.01); *B01D 2257/302* (2013.01); *B01D 2257/304* (2013.01); *B01D 2257/406* (2013.01); *B01D 2257/504* (2013.01); *B01D 2257/7022* (2013.01); *B01J 29/035* (2013.01); *B01J 2229/42* (2013.01); *C07B 2200/13* (2013.01); *Y02C 10/08* (2013.01); *Y02P 20/152* (2015.11)

(56) References Cited

U.S. PATENT DOCUMENTS

| | | | |
|---|---|---|---|
| 2011/0166177 | A1 | 7/2011 | Holtman et al. |
| 2014/0336394 | A1* | 11/2014 | Burton ............... B01J 29/70 548/524 |
| 2015/0158020 | A1* | 6/2015 | Nicholas ............. B01J 29/70 423/704 |
| 2015/0329487 | A1* | 11/2015 | Schmitt ............... C07D 207/06 208/107 |
| 2016/0131972 | A1* | 5/2016 | Fukushima ........... G03F 7/0045 430/270.1 |

OTHER PUBLICATIONS

The International Search Report and Written Opinion of PCT/US2016-063444 dated Feb. 10, 2017.

Ren et al., "Smart anti-microbial composite coatings for textiles and plastics", Science Direct, Functional Textiles for Improved Performance, Protection and Health, (2011).

\* cited by examiner

EMM-28, A NOVEL SYNTHETIC CRYSTALLINE MATERIAL, ITS PREPARATION AND USE

CROSS-REFERENCE TO RELATED APPLICATIONS

This application is a divisional application filed under 37 C.F.R. 1.53(b) of parent U.S. patent application Ser. No. 15/359,644, the entirety of which is hereby incorporated herein by reference, and claims priority to U.S. Non-Provisional patent application Ser. No. 15/359,644 filed on Nov. 23, 2016 which claims priority to U.S. Provisional Application Ser. No. 62/262,950 filed on Dec. 4, 2015, also herein incorporated by reference in its entirety.

FIELD

This invention relates to a novel synthetic crystalline material, EMM-28, and to a method for its preparation. This invention also relates to the use of porous forms of EMM-28 in organic conversion and sorption processes.

BACKGROUND

Zeolitic materials are known to have utility as sorbents and to have catalytic properties for various types of hydrocarbon conversion reactions. Certain zeolitic materials are ordered, porous crystalline materials having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for sorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates and substituted silicates, in which the silicon is partially or completely replaced by other tetravalent elements. These silicates can be described as a rigid three-dimensional framework of $SiO_4$ tetrahedra and optionally tetrahedra of a trivalent element oxide, e.g., $AlO_4$ and/or $BO_4$, in which the tetrahedra are cross-linked by the sharing of oxygen atoms whereby the local ratio of the total trivalent element and silicon atoms to oxygen atoms is 1:2. The electrovalence of the tetrahedra containing the trivalent element is balanced by the inclusion in the crystal of a cation, for example, an alkali metal or an alkaline earth metal cation. This can be expressed wherein the ratio of the trivalent element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and beta. An intermediate pore size zeolite generally has a pore size from about 5 Å to less than 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite-1, and silicalite-2. A small pore size zeolite has a pore size from about 3 Å to less than 5 Å and includes, for example, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

Many zeolites are synthesized in the presence of an organic structure directing agent, such as an organic nitrogen compound. For example, ZSM-5 may be synthesized in the presence of tetrapropylammonium cations and zeolite MCM-22 may be synthesized in the presence of hexamethyleneimine. It is also known to synthesize zeolites and related molecular sieves in the presence of diquaternary directing agents. For example, U.S. Published Patent Application No. 2010/0178241 discloses the synthesis of EU-1 in the presence of hexamethonium cations.

According to the present invention, a new zeolite structure, designated EMM-28 and having a unique X-ray diffraction pattern, has now been synthesized using as an organic structure directing agent a novel diquat with N-methylpyrrolidinium groups connected to a phenyl ring by a linear polymethylene group of the formula $(CH_2)_3$ at the 1,3-positions (meta) or at the 1,4-positions (para).

SUMMARY

In a first aspect, the invention resides in a synthetic crystalline material having, in its as-calcined form, an X-ray diffraction pattern including the following peaks in Table 1:

TABLE 1

| d-spacing (Å) | Relative Intensity (I/Io × 100) |
|---|---|
| 19.85 ± 0.30 | W |
| 11.20 ± 0.30 | VS |
| 9.97 ± 0.20 | W |
| 8.80 ± 0.10 | M |
| 6.86 ± 0.10 | W |
| 6.49 ± 0.10 | VW |
| 5.85 ± 0.10 | VW |
| 5.70 ± 0.10 | VW |
| 5.61 ± 0.10 | VW |
| 5.12 ± 0.10 | VW |
| 4.60 ± 0.05 | VW |
| 4.45 ± 0.05 | VW |
| 4.33 ± 0.05 | M-S |
| 4.25 ± 0.05 | VW-W |
| 4.15 ± 0.05 | VW-W |
| 4.06 ± 0.05 | VW |
| 3.98 ± 0.05 | VW |
| 3.88 ± 0.05 | VW |
| 3.76 ± 0.05 | VW-W |
| 3.73 ± 0.05 | VW-W |
| 3.68 ± 0.05 | W |
| 3.53 ± 0.05 | W |
| 3.43 ± 0.05 | W |

TABLE 1-continued

| d-spacing (Å) | Relative Intensity (I/Io × 100) |
|---|---|
| 3.28 ± 0.05 | W-M |
| 3.19 ± 0.05 | VW |
| 3.16 ± 0.05 | VW |
| 3.11 ± 0.05 | VW |
| 3.07 ± 0.05 | VW |
| 2.94 ± 0.025 | VW |
| 2.79 ± 0.025 | VW |
| 2.60 ± 0.025 | VW |
| 2.53 ± 0.025 | VW |
| 2.50 ± 0.025 | VW |
| 2.46 ± 0.025 | VW |
| 2.41 ± 0.025 | VW |
| 2.34 ± 0.025 | VW |

In a second aspect, the invention resides in a synthetic crystalline material having, in its as-synthesized form, an X-ray diffraction pattern including the following peaks in Table 2:

TABLE 2

| d-spacing (Å) | Relative Intensity (I/Io × 100) |
|---|---|
| 20.00 ± 0.30 | W |
| 11.56 ± 0.30 | VS |
| 10.03 ± 0.20 | W |
| 8.87 ± 0.20 | W-M |
| 6.91 ± 0.10 | W |
| 6.66 ± 0.10 | VW |
| 6.03 ± 0.10 | VW |
| 5.70 ± 0.10 | VW |
| 5.55 ± 0.10 | VW |
| 5.14 ± 0.10 | W-M |
| 4.64 ± 0.05 | W |
| 4.43 ± 0.05 | VS |
| 4.36 ± 0.05 | S-VS |
| 4.28 ± 0.05 | W-M |
| 4.16 ± 0.05 | M |
| 4.00 ± 0.05 | VW |
| 3.93 ± 0.05 | W |
| 3.84 ± 0.05 | M |
| 3.77 ± 0.05 | M |
| 3.70 ± 0.05 | M |
| 3.54 ± 0.05 | VW |
| 3.45 ± 0.05 | M |
| 3.31 ± 0.05 | M-S |
| 3.25 ± 0.05 | VW-W |
| 3.17 ± 0.05 | VW |
| 3.12 ± 0.05 | VW |
| 3.00 ± 0.05 | VW |
| 2.96 ± 0.025 | VW |
| 2.84 ± 0.025 | VW |
| 2.79 ± 0.025 | VW |
| 2.76 ± 0.025 | VW |
| 2.63 ± 0.025 | VW |
| 2.57 ± 0.025 | VW |
| 2.47 ± 0.025 | VW |
| 2.36 ± 0.025 | VW |
| 2.34 ± 0.025 | VW |

In a third aspect, the invention resides in a synthetic porous crystalline material having within its pore structure a dication having formula (I) or (II):

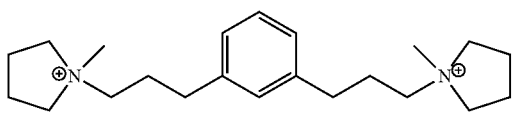

(I)

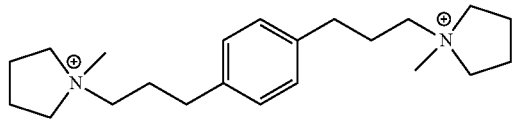

(II)

In a fourth aspect, the invention resides in an organic nitrogen compound comprising a dication having formula (I), (II) or (III):

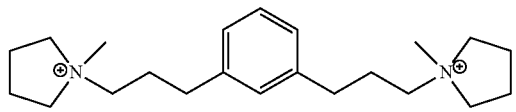

(I)

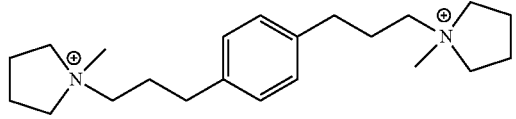

(II)

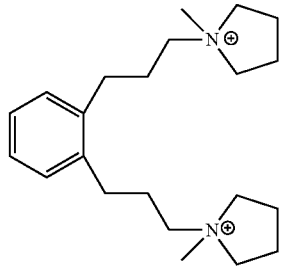

(III)

In a fifth aspect, the invention resides in a method of producing a 1,1'-(1,x-phenylenebis(propane-3,1-diyl))bis(1-methylpyrrolidin-1-ium) compound, where x is 2, 3 or 4, the method comprising:

reacting 1,x-bis(halomethyl)benzene with a dialkyl malonate to produce a tetraalkyl 2,2'-(1,x-phenylenebis (methylene))dimalonate;

converting at least part of the tetraalkyl 2,2'-(1,x-phenylenebis(methylene))dimalonate to 3,3'-(1,x-phenylene)dipropanoic acid;

reducing at least part of the 3,3'-(1,x-phenylene)dipropanoic acid, or an ester thereof, to 3,3'-(1,x-phenylene)bis (propan-1-ol));

reacting at least part of the 3,3'-(1,x-phenylene)bis(propan-1-ol)) with an alkyl- or aryl-sulfonyl halide to produce the corresponding sulfonate diester;

reacting at least part of the sulfonate diester with pyrrolidine to produce 1,x-bis(3-(pyrrolidin-1-yl)propyl)benzene; and reacting at least part of the 1,x-bis(3-(pyrrolidin-1-yl) propyl)benzene with a methyl halide to produce a 1,1'-(1, x-phenylenebis(propane-3,1-diyl))bis(1-methylpyrrolidin-1-ium) compound.

In another illustration of the fifth aspect, the invention resides in a method of producing a 1,1'-(1,x-phenylenebis (propane-3,1-diyl))bis(1-methylpyrrolidin-1-ium) compound, where x is 2, 3 or 4, the method comprising:

reacting at least part of the sulfonate diester of 3,3'-(1,x-phenylene)bis(propan-1-ol)) with 1-methylpyrrolidine to produce a 1,1'-(1,x-phenylenebis(propane-3,1-diyl))bis(1-methylpyrrolidin-1-ium) compound.

In a sixth aspect, the invention resides in a method of producing a 1,1'-(1,x-phenylenebis(propane-3,1-diyl))bis(1-methylpyrrolidin-1-ium) compound, where x is 2, 3 or 4, the method comprising:

reacting 1-(prop-2-yn-1-yl)pyrrolidine with a 1,x-dihalo-substituted benzene to produce a compound of formula (IVA), (IVB) or (IVC):

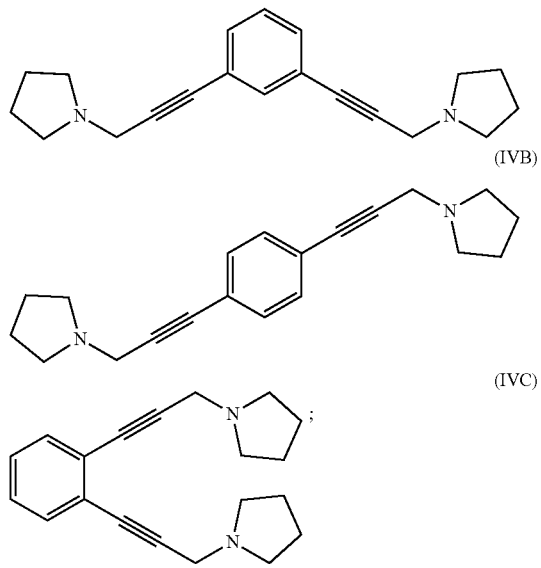

hydrogenating at least part of the compound of formula (IVA), (IVB) or (IVC) to produce a compound of formula (VA), (VB) or (VC), respectively:

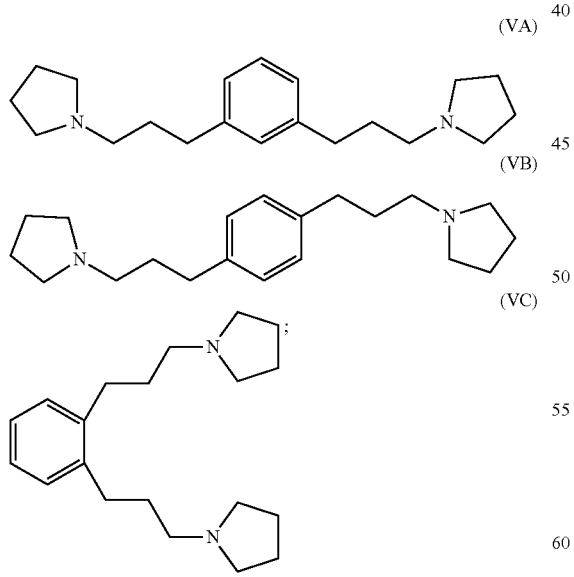

and reacting at least part of the compound of formula (VA), (VB) or (VC) with a methyl halide to produce a 1,1'-(1,x-phenylenebis(propane-3,1-diyl))bis(1-methylpyrrolidin-1-ium) compound.

In a seventh aspect, the invention resides in a method of producing a 1,1'-(1,x-phenylenebis(propane-3,1-diyl))bis(1-methylpyrrolidin-1-ium) compound, where x is 2, 3 or 4, the method comprising:

reacting a compound of formula (VI)

where $R^1$ is a hydroxyl group or an alkyl- or aryl-sulfonate group, with 1,x-dihalo-substituted benzene to produce a compound of formula (VIIA), (VIIB) or (VIIC):

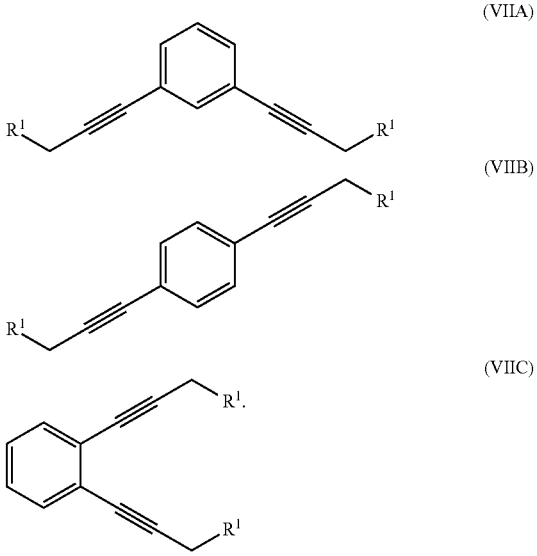

In one illustration of the seventh aspect, $R^1$ is an alkyl- or aryl-sulfonate group and the method further comprises:

hydrogenating at least part of the compound of formula (VIIA), (VIIB) or (VIIC) to produce a compound of formula (VIIIA), (VIIIB) or (VIIIC), respectively:

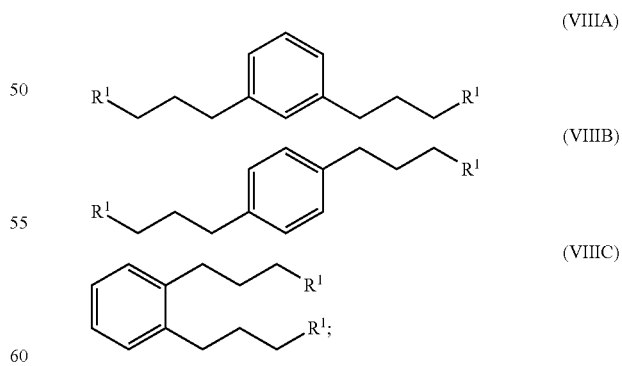

and converting at least part of the compound of formula (VIIIA), (VIIIB) or (VIIIC) to a 1,1'-(1,x-phenylenebis(propane-3,1-diyl))bis(1-methylpyrrolidin-1-ium) compound by (i) reaction with 1-methylpyrrolidine or (ii) by reaction with pyrrolidine and then with a methyl halide.

In another illustration of the seventh aspect, $R^1$ is an alkyl- or aryl-sulfonate group and the method further comprises:

reacting at least part of the compound of formula (VIIA), (VIIB) or (VIIC) with pyrrolidine to produce a compound of formula (IVA), (IVB) or (IVC), respectively:

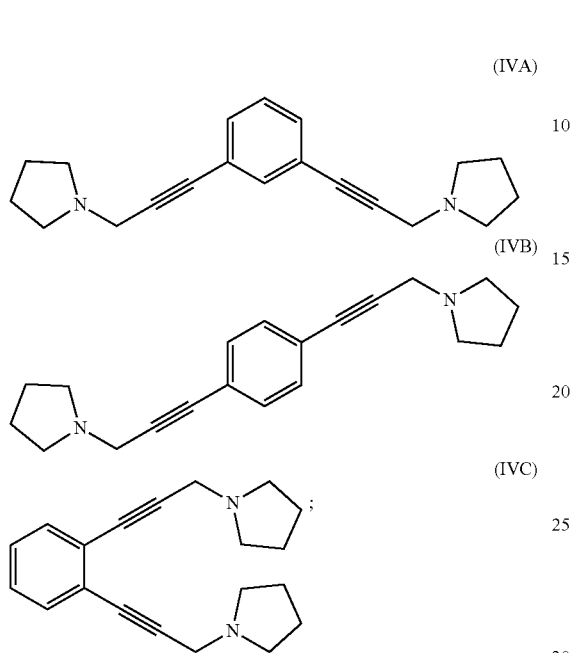

(IVA)

(IVB)

(IVC)

hydrogenating at least part of the compound of formula (IVA), (IVB) or (IVC) to produce a compound of formula (VA), (VB) or (VC), respectively:

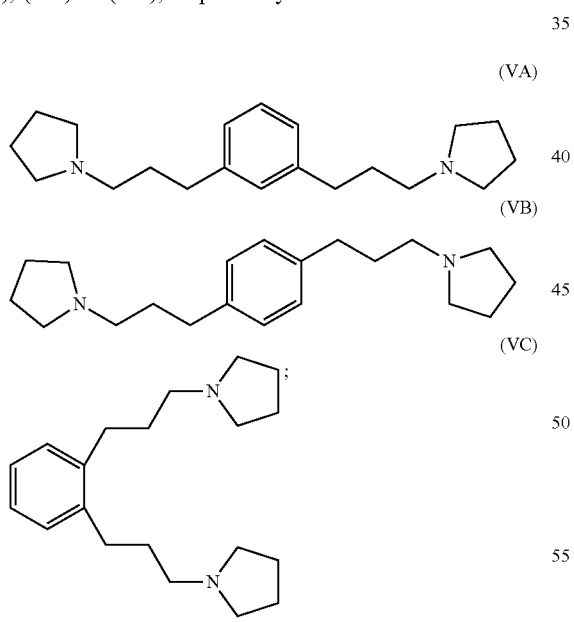

(VA)

(VB)

(VC)

and reacting at least part of the compound of formula (VA), (VB) or (VC) with a methyl halide to produce a 1,1'-(1,x-phenylenebis(propane-3,1-diyl))bis(1-methylpyrrolidin-1-ium) compound.

In a further illustration of the seventh aspect, $R^1$ is a hydroxyl group and the method further comprises:

reacting at least part of the compound of formula (VIIA), (VIIB) or (VIIC) with an alkyl- or aryl-sulfonyl halide such as p-toluenesulfonyl chloride to produce a compound of formula (IXA), (IXB) or (IXC), respectively:

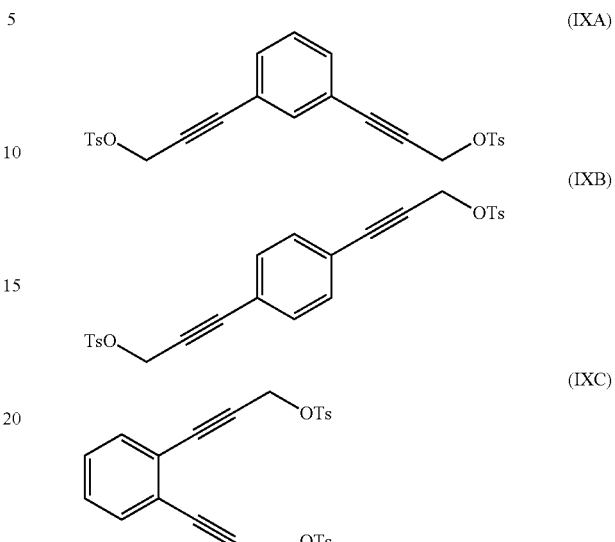

(IXA)

(IXB)

(IXC)

The compound of formula (IXA), (IXB) or (IXC) may then be hydrogenated to produce a compound of formula (XA), (XB) or XC, respectively:

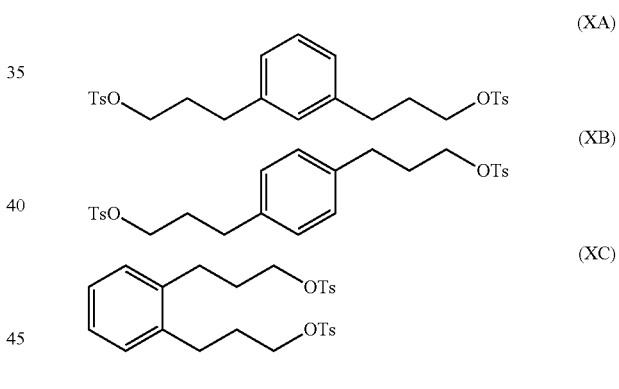

(XA)

(XB)

(XC)

which may then be converted into a 3,3-(1,x-phenylene)bis(propane-3,1-diyl)bis(1-methylpyrrolidinium) compound by (i) reaction with 1-methylpyrrolidine or (ii) by reaction with pyrrolidine and then with a methyl halide.

In an eighth aspect, the invention resides in a method of producing a 1,1'-(1,x-phenylenebis(propane-3,1-diyl))bis(1-methylpyrrolidin-1-ium) compound, where x is 2, 3 or 4, the method comprising:

reacting a compound of formula (VI)

$$\equiv\!\!-\!\!\diagdown\!\! R^1 \quad (VI)$$

where $R^1$ is a hydroxyl group, with 1,x-dihalo-substituted benzene to produce a compound of formula (VIIA), (VIIB) or (VIIC):

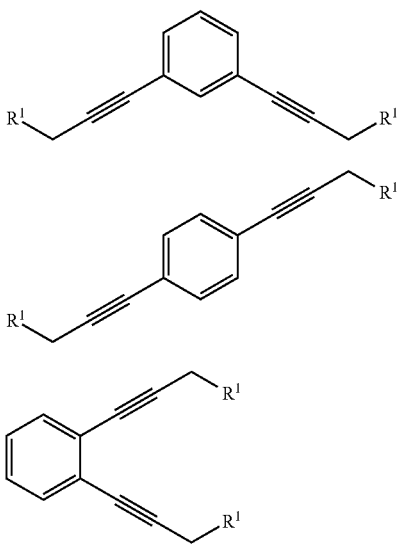

(VIIA)

(VIIB)

(VIIC)

hydrogenating at least part of the compound of formula (VIIA), (VIIB) or (VIIC) to produce a compound of formula (VIIIA), (VIIIB) or (VIIIC), respectively:

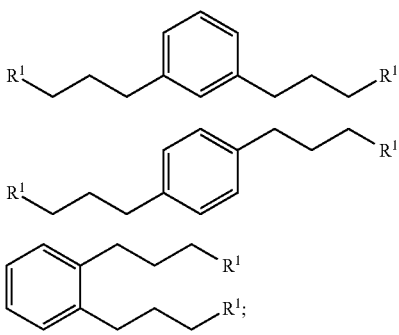

(VIIIA)

(VIIIB)

(VIIIC)

and reacting at least part of the compound of formula (VIIIA), (VIIIB) or (VIIIC) with an alkyl- or aryl-sulfonyl halide such asp-toluenesulfonyl chloride to produce a compound of formula (XA), (XB) or XC, respectively:

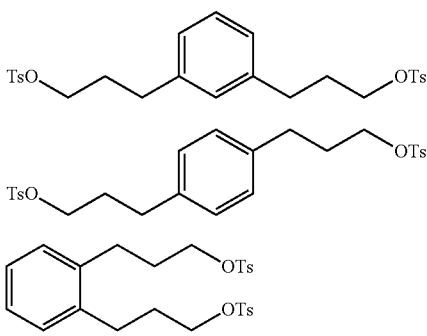

(XA)

(XB)

(XC)

converting at least part of the compound of formula (XA), (XB) or (XC) to a 1,1'-(1,x-phenylenebis(propane-3,1-diyl)) bis(1-methylpyrrolidin-1-ium) compound by (i) reaction with 1-methylpyrrolidine or (ii) by reaction with pyrrolidine and then with a methyl halide.

DETAILED DESCRIPTION OF THE EMBODIMENTS

Described herein is a novel molecular sieve material, designated EMM-28, its synthesis in the presence of an organic structure directing agent comprising one or more novel diquaternary ammonium compounds, and its use as a sorbent and a catalyst for organic conversion reactions. Methods of producing the novel diquaternary ammonium compounds are also disclosed.

Molecular Sieve Material EMM-28

The novel molecular sieve material EMM-28 is characterized by an X-ray diffraction pattern which, in the calcined form of the molecular sieve, includes at least the peaks set out in Table 1 above and which, in the as-synthesized form of the molecular sieve, includes at least the peaks set out in Table 2 above.

The X-ray diffraction data reported herein were collected with a PANalytical X-Pert Pro diffraction system, equipped with an X'Celerator detector, using copper K-alpha radiation. The diffraction data were recorded by step-scanning at 0.017 degrees of two-theta, where theta is the Bragg angle, and a counting time of 21 seconds for each step. The interplanar spacings, d-spacings, were calculated in Angstrom units, and the relative peak area intensity of the lines, I/I(o), is one-hundredth of the intensity of the strongest line, above background, were determined with the MDI Jade peak profile fitting algorithm. The intensities are uncorrected for Lorentz and polarization effects. The relative intensities are given in terms of the symbols VS=very strong (greater than 60 to 100), S=strong (greater than 40 to 60), M=medium (greater than 20 to 40), W=weak (10 to 20) and VW=very weak (less than 10). In some embodiments, some or all the lines designated as "very weak" can have a relative intensity greater than zero.

It should be understood that diffraction data listed for this sample as single lines may consist of multiple overlapping lines which under certain conditions, such as differences in crystallography, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

Figure 1:
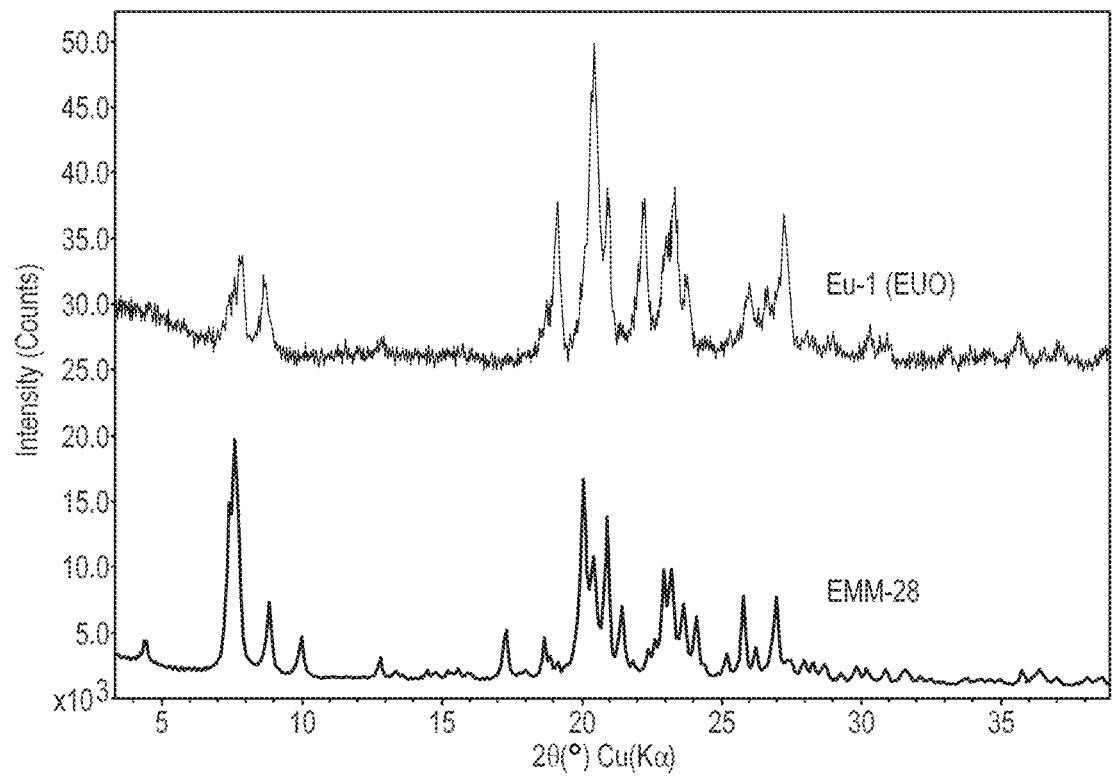
FIG. 1 compares the X-ray diffraction patterns of the as-synthesized EMM-28 produced in Example 8 and the as-synthesized EU-1 material produced in Example 9.

The X-ray diffraction patterns of EMM-28 have qualitative similarities with those of EUO-type materials (e.g., EU-1 and/or ZSM-50). A comparison of the powder XRD patterns is shown below (FIG. 1). The broad features of the experimental pattern of EMM-28 appear to be caused by the thin crystal morphologies (see FIG. 2). The similarity of the powder XRD patterns suggest that the framework of EMM-28 might be related to but distinct from EUO.

In its calcined form, molecular sieve EMM-28 has a chemical composition comprising the molar relationship:

$$(n)X_2O_3:YO_2$$

wherein n is a number less than 0.05, such as less than 0.025, for example less than 0.01, such as less than 0.005, for example less than 0.001, such as less than 0.0005, for example less than 0.00025, X is a trivalent element, such as one or more of B, Al, Fe, and Ga, especially Al, and Y is a tetravalent element, such as Si, Ge, Sn, Ti, and Zr, especially Ge and/or Si. It will be appreciated from the permitted values for n that EMM-28 can be synthesized in totally siliceous form in which the trivalent element X is absent or essentially absent.

In its as-synthesized form, molecular sieve EMM-28 may have a chemical composition comprising the molar relationship:

$$(m)M:(b)Q:(n)X_2O_3:YO_2:(z)H_2O$$

wherein m is a number having a value equal to or greater than 0 to less than or equal to 0.1, b is a number having a value greater than 0 to less than or equal to 0.05, n is a number less than 0.025, for example less than 0.001, such as less than 0.0005, for example less than 0.00025, and z is a number having a value greater than or equal to 0 to less than or equal to 0.2, and wherein M is an alkali metal cation, X is a trivalent element, such as one or more of B, Al, Fe, and Ga, especially Al, Y is a tetravalent element, such as Si, Ge, Sn, Ti, and Zr or mixtures thereof, especially Ge and/or Si and Q is an organic structure directing agent.

In another embodiment, the as-synthesized form of EMM-28 may have a chemical composition comprising the molar relationship:

$$(k)F:(b)Q:(n)X_2O_3:YO_2:(z)H_2O$$

wherein k is a number having a value equal to or greater than 0 to less than or equal to 0.01, b is a number having a value greater than 0 to less than or equal to 0.05, n is a number less than 0.025, for example less than 0.001, such as less than 0.0005, for example less than 0.00025, and z is a number having a value greater than or equal to 0 to less than or equal to 0.2, and wherein F is a fluoride ion, X is a trivalent element, such as one or more of B, Al, Fe, and Ga, especially Al, Y is a tetravalent element, such as Si, Ge, Sn, Ti, and Zr or mixtures thereof, especially Ge and/or Si and Q is an organic structure directing agent.

In one embodiment, Q is selected from one or more of 1,1'-(1,3-phenylenebis(propane-3,1-diyl))bis(1-methylpyrrolidin-1-ium) dication and 1,1'-(1,4-phenylenebis(propane-3,1-diyl))bis(1-methylpyrrolidin-1-ium) dication having the formula I (meta) and II (para) respectively:

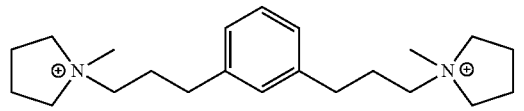
(I)

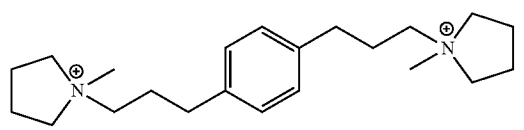
(II)

The Q component, which is associated with the as-synthesized material as a result of its presence during crystallization, can easily be removed by conventional post-crystallization methods.

The molecular sieve EMM-28 is thermally stable and in its calcined form exhibits a high surface area and significant hydrocarbon sorption capacity. Representative sorption capacities and relative sorption rates are listed below:

| Adsorbate | Capacity | Relative Sorption Rate |
|---|---|---|
| Nitrogen | 0.17 cc/g | Fast |
| n-Hexane | 0.089 g/g | Fast |
| 2,3-Dimethylbutane | 0.077 g/g | Fast |
| 2,2-Dimethylbutane | 0.044 g/g | Slow |

EMM-28 can be prepared from a synthesis mixture comprising sources of water, hydroxyl ions, an oxide of a tetravalent element Y, optionally a trivalent element X, optionally a source of fluoride (F⁻) ions, and the organic structure directing agent (Q) described above, the mixture having a composition, in terms of mole ratios of oxides, within the following ranges:

| Reactants | Useful | Advantageous |
|---|---|---|
| $X_2O_3/YO_2$. | 0 to 0.05 | 0 to 0.01 |
| $H_2O/YO_2$ from | 2 to 100 | 4 to 40 |
| $OH^-/YO_2$ | 0.05 to 0.6 | 0.10 to 0.40 |
| $Q/YO_2$ | 0.04 to 0.60 | 0.10 to 0.5 |
| $F/YO_2$ | 0 to 0.25 | 0 to 0.1 |

Suitable sources of the tetravalent element Y depend on the element Y selected; but in the preferred embodiments, in which Y is silicon and/or germanium, include colloidal suspensions of silica, precipitated silica, fumed silica, alkali metal silicates, tetraalkyl orthosilicates and germanium oxide. If present, the trivalent element X is normally aluminum and suitable sources of aluminum include hydrated alumina, aluminum hydroxide, alkali metal aluminates, aluminum alkoxides, and water-soluble aluminum salts, such as aluminum nitrate. If present, suitable sources of fluoride ions include one or more of HF, $NH_4F$, and $NH_4HF_2$.

Suitable sources of Q are the hydroxides and/or salts of the relevant diquaternary ammonium compounds. The compounds themselves are believed to be novel, and can be synthesized from 1,3-bis(halomethyl)benzenes (for compounds of formula I) and from 1,4-bis(halomethyl)benzenes (for compounds of formula II) according to the procedure described below. In addition, the compounds of formula I and II can be prepared by reaction of 1,3- and 1,4-dihalobenzenes with certain propyne derivatives using the Sonogashira coupling reaction. Again this mode of synthesis is discussed in more detail below. Similar reactions starting from 1,2-bis(halomethyl)benzenes and 1,2-dihalobenzenes, can be used to produce the ortho-isomer of the compounds of formula I and II, namely 1,1'-(1,2-phenylenebis(propane-3,1-diyl))bis(1-methylpyrrolidin-1-ium) dication having the formula III below:

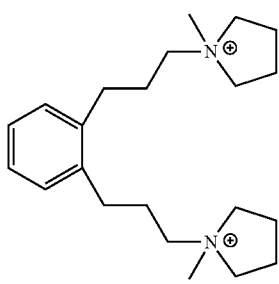 (III)

The reaction mixture for producing the molecular sieve EMM-28 may also contain seeds of a crystalline material, such as EMM-28 from a previous synthesis, desirably in an amount from 0.01 ppm by weight to 500,000 ppm by weight, such as from 100 ppm by weight to 5,000 ppm by weight of the reaction mixture.

The reagents are typically mixed together by a mechanical process such as stirring or high shear blending to assure suitable homogenization of the synthesis mixture. Depending on the nature of the reagents it may be necessary to reduce the amount of water in the mixture before crystallization to obtain the preferred $H_2O/YO_2$ molar ratio. Suitable methods for reducing the water content are evaporation under a static or flowing atmosphere such as ambient air, dry nitrogen, dry air, or by spray drying or freeze drying.

Crystallization of EMM-28 can be carried out at either static or stirred conditions in a suitable reactor vessel, such as for example, polypropylene jars or Teflon lined or stainless steel autoclaves, at a temperature of about 100° C. to about 200° C. for a time sufficient for crystallization to occur at the temperature used, e.g., from about 1 day to about 14 days. Thereafter, the crystals are separated from the liquid and recovered.

To the extent desired and depending on the $X_2O_3/YO_2$ molar ratio of the material, any cations in the as-synthesized EMM-28 can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The molecular sieve described herein may be subjected to treatment to remove part or all of the organic structure directing agent Q used in its synthesis. This is conveniently effected by thermal treatment in which the as-synthesized material is heated at a temperature of at least about 370° C. for at least 1 minute and generally not longer than 20 hours. While sub-atmospheric pressure can be employed for the thermal treatment, atmospheric pressure is desired for reasons of convenience. The thermal treatment can be performed at a temperature up to about 925° C. The thermally-treated product, especially in its metal, hydrogen and ammonium forms, is particularly useful in the catalysis of certain organic, e.g., hydrocarbon, conversion reactions.

The present molecular sieve may be intimately combined with a hydrogenating component, such as molybdenum, tungsten, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The present molecular sieve, when employed either as a sorbent or as a catalyst should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the EMM-28 in a vacuum, but a longer time is required to obtain a sufficient amount of dehydration.

The present molecular sieve can be used as a sorbent or, particularly in its aluminosilicate form, as a catalyst to catalyze a wide variety of organic compound conversion processes including many of present commercial/industrial importance. Examples of chemical conversion processes which are effectively catalyzed by the crystalline material of this invention, by itself or in combination with one or more other catalytically active substances including other crystalline catalysts, include those requiring a catalyst with acid activity. Examples of organic conversion processes which may be catalyzed by EMM-28 include cracking, hydrocracking, disproportionation, alkylation, oligomerization, and isomerization.

As in the case of many catalysts, it may be desirable to incorporate EMM-28 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with EMM-28, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with EMM-28 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with EMM-28 also include inorganic oxides, such as silica, zirconia, titania, magnesia, beryllia, alumina, and mixtures thereof.

In addition to the foregoing materials, EMM-28 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of EMM-28 and inorganic oxide matrix may vary widely, with the EMM-28 content ranging from about 1 to about 90 percent by weight, and more usually, particularly when the composite is prepared in the form of beads, in the range of about 2 to about 80 weight percent of the composite.

EXAMPLES

The invention will now be more particularly described with reference to the following non-limiting Examples and the accompanying drawings.

Synthesis of Organic Structure Directing Agents (Formulas I, II, and III)

As discussed above, the organic structure directing agents, Q, useful in the synthesis of EMM-28 can be produced from 1,3-bis(halomethyl)benzenes (for compounds of formula I) and from 1,4-bis(halomethyl)benzenes (for compounds of formula II).

A suitable synthesis regimen for a compound of formula I from 1,3-bis(chloromethyl)benzene is described below.

Preparation of 3,3'-(1,3-phenylene)dipropionic acid

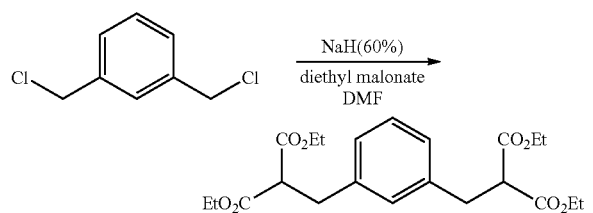

An oven dried 2 L 3-necked jacketed flask equipped with mechanical stirrer was assembled hot, and cooled under flowing $N_2$ then charged with 67.2 g (1680 mmol) 60% sodium hydride in mineral oil. The contents were cooled to 0° C. with circulating glycol-water and 670 mL anhydrous DMF added via cannula. 360 mL (2.37 mole) diethylmalonate was added dropwise to the flask over 40 minutes. About half way through the addition, the chiller was drained and the temperature allowed to rise to 35° C. All the NaH had dissolved and the solution was clear. To this was added 102.1 g (582 mmol) 1,3-bis(chloromethyl)benzene all at once. The temperature rose to 65° C. and solid formed. After heating with steam for 1 hour, the flask was cooled to 0° C. and a solution of 37 mL concentrated HCl in 1000 mL $H_2O$ was added. The contents of the flask were then transferred to a separatory funnel, where the viscous lower layer was withdrawn as product. After removing volatiles on a rotary evaporator, the product was distilled at 125° C. @ 250 mTorr to produce 228 g (86%) white liquid product.

Preparation of tetraethyl 2,2'-(1,3-phenylenebis(methylene))dimalonate

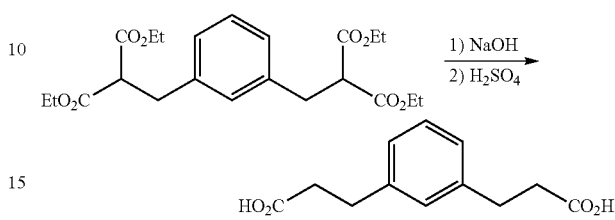

The 3,3'-(1,3-phenylene)dipropionic acid was poured into 121 g (3.02 mol) NaOH in 640 mL $H_2O$ and washed with 25 mL ethanol. The mixture was heated at reflux for 45 min (homogeneous when it reached reflux) then 325 mL was distilled through a 6" Vigreux column. The boiling point of the last 100 mL was 100-101° C. The solution was cooled and 152 g concentrated $H_2SO_4$ dripped in at a rate to just maintain reflux. A bubbler was added and the mixture was heated at reflux until no more $CO_2$ evolved (overnight). There was yellow oil floating in the flask plus some solid. The mixture was poured into 2 L $H_2O$, extracted 2×200 mL diethylether, then the extract was washed 1×200 mL with saturated NaCl and filtered through 4 Å molecular sieve. The solvent was removed on a rotary evaporator and the remaining volatiles distilled at 120° C. at 260 mTorr to give 110.5 g (100%) pale tan wax. The product had the expected $^{13}C$ NMR and $^1H$ NMR spectra. $^{13}C$ NMR(CDCl$_3$): δ 174.2($C_q$), 141.3($C_q$), 128.7(CH), 128.6(CH), 126.3(CH), 35.7(CH$_2$), 30.8(CH). $^1H$ NMR(CDCl$_3$): δ 12.12(s, 1.9H), 7.19(m, 1.1H), 7.05(m, 3.2H), 2.80(t, 3.9H), 2.53(t, 3.8H).

Preparation of 3,3'-(1,3-phenylene)bis(propan-1-ol)

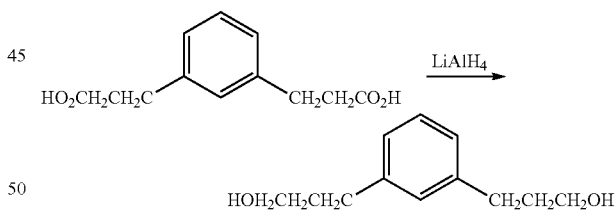

An oven dried 3 L 3-necked jacketed flask equipped with equalizing dropping funnel, reflux condenser, and mechanical stirrer was assembled hot and cooled under flowing $N_2$ then charged with 920 g anhydrous THF and 30.55 g (805 mmol) LiAlH$_4$ pellets. The mixture was stirred for 30 min then 110 g (498 mmol) of tetraethyl 2,2'-(1,3-phenylenebis (methylene))dimalonate in 250 g anhydrous THF was added dropwise over 1 hour. Three quarters of the way through the addition the solid became very hard to stir. Addition of 300 mL anhydrous THF made the slurry stirrable again. The reaction was exothermic throughout the addition and produced gas ($H_2$) throughout the addition. The mixture was refluxed 20 min, cooled to 0° C. and quenched with 150 mL 1:1 v/v $H_2O$:THF then 42.7 g NaOH in 427 g $H_2O$. The product was filtered through a Buchner funnel and the solid residue washed with 500 mL diethylether. After removal of the solvent on a rotary evaporator, remaining volatiles were removed by vacuum distillation at 100° C. @ 2 mTorr to give 70.2 g (74%) white, semisolid. The product had the expected $^{13}$C NMR and $^1$H NMR spectra. $^{13}$C NMR (CDCl$_3$): δ 142.0(C$_q$), 128.7(CH), 128.4(CH), 125.9(CH), 61.9(CH$_2$), 34.2(CH$_2$), 32.0(CH$_2$). $^1$H NMR(CDCl$_3$): δ 7.20 (m, 1.2H), 7.04(m, 3.3H), 3.64(m, 3.8H), 3.05(b, 1.8H), 2.68(m, 4.1H), 1.89(m, 3.8H).

Preparation of 1,3-phenylenebis(propane-3,1-diyl) bis(4-methylbenzenesulfonate)

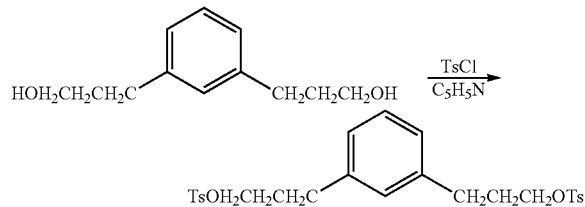

A 1 L jacketed flask containing 70.2 g (362 mmol) of 3,3'-(1,3-phenylene)bis(propan-1-ol), 260 mL pyridine, and 480 mL CHCl$_3$ (amylene stabilized) was cooled to −5° C. with circulating glycol-water and 138 g (723 mmol) p-toluenesulfonyl chloride added all at once. The temperature rose to 25° C., chilling was stopped and, after stirring for 45 min, the mixture was poured into 1000 mL H$_2$O+212 mL conc. HCl. The lower layer was separated and washed with 100 mL saturated NaCl solution. Residual solvent was removed on a rotary evaporator, and the remaining volatiles were removed by vacuum distillation at 60° C. @ 650 mTorr to give 171 g (94%) brown resin. The product had the expected $^{13}$C NMR and $^1$H NMR spectra. $^{13}$C NMR(CDCl$_3$): δ 144.8 (C$_q$), 140.6(CH), 133.0(CH), 129.0(CH), 127.8(CH), 126.3 (CH), 69.8(CH$_2$), 31.4(CH$_2$), 30.3(CH$_2$), 21.6(CH$_3$). $^1$H NMR(CDCl$_3$): δ 7.81(d, 4.1H), 7.36(d, 3.8H), 7.13(m, 1.4H), 6.90(m, 3.3H), 4.04(t, 4.1H), 2.61(t, 4.7H), 2.46(s, 4.7H), 1.94(m, 4.1H).

Preparation of 1,3-bis(3-(pyrrolidin-1-yl)propyl)benzene

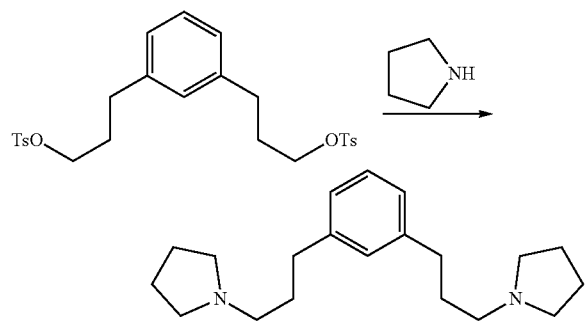

116 g (231 mmol) of 1,3-phenylenebis(propane-3,1-diyl) bis(4-methylbenzenesulfonate) was treated with 160 mL (1.92 mol) pyrrolidine. The mixture darkened and an exotherm took the temperature to boiling. The mixture was poured, hot, into 800 mL H$_2$O containing 80 g NaOH. The layers separated and the aqueous layer was extracted with 1×350 mL diethylether. The organic layers were combined, washed 1×200 mL H$_2$O, and the volatiles removed on a rotary evaporator before the product was distilled at 220° C. @ 180 mTorr to give 54.9 g yellow oil plus solid. GCMS shows the expected product with m/z=300 (large M-1 peak) but it is heavily contaminated with 1-tosylpyrrolidine. The product is estimated to be 77% from $^1$H NMR and 81% from $^{13}$C NMR so overall yield about 140 mmol. The $^{13}$C NMR is consistent with the expected product plus 1-tosylpyrrolidine.

Preparation of 1,1'-(1,3-phenylenebis(propane-3,1-diyl))bis(1-methylpyrrolidin-1-ium) hydroxide

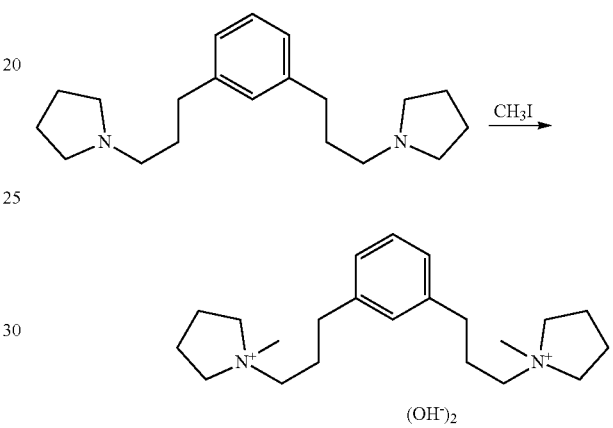

The 1,3-bis(3-(pyrrolidin-1-yl)propyl)benzene was dissolved in 150 mL acetone in an Erlenmeyer flask and 40 mL (680 mmol) iodomethane added gradually over about 15 min. The solution reached gentle reflux and much solid precipitated. The flask was stoppered, wrapped in Al foil, allowed to stand for two days at room temperature, filtered, washed with diethylether, and dried to constant weight at 65° C. to give 77.3 g pink solid (94% based on estimated purity of diamine). This was ion exchanged in batch mode to give 371 g pale yellow solution. Titration of 2.62 mL of this solution diluted to 25 mL took 6.19 mL to titrate 91.1 mg potassium phthalate. This calculates for 12.5% as the dihydroxide. Integration of the $^1$H NMR organic hydrogen signals against water signal gave 12.7% as the dihydroxide. The product had the expected $^{13}$C NMR, $^1$H NMR, and $^{14}$N NMR spectra. $^{13}$C NMR(d$_6$-DMSO): δ 141.1(C$_q$), 129.0 (CH), 128.9(CH), 126.6(CH), 64.0(CH$_2$), 63.2(CH$_2$), 48.3 (CH$_3$), 32.2(CH$_2$), 25.3(CH$_2$), 21.6(CH$_2$). $^1$H NMR(D$_2$O): δ 7.25(m, 2.1H), 7.14(m, 2.1H), 3.48(m,12.2H), 3.04(s, 5.9H), 2.62(t,3.9H), 2.07 (m,11.8H) $^{14}$N NMR(D$_2$O): δ 52.6(⊗v$_{1/2}$=8 Hz, calculated shift 54.0 ppm).

In a modification of the above synthesis regimen for the dication of formula I, 1,3-phenylenebis(propane-3,1-diyl)bis (4-methylbenzenesulfonate) is reacted with 1-methylpyrrolidine in chloroform or acetonitrile to produce the dication directly without intermediate production of the diamine.

Additionally and alternatively, another suitable synthesis regimen for a compound of formula I from 1,3-diiodobenzene is described below.

Preparation of 3,3'-(1,3-phenylene)bis(prop-2-yn-1-ol)

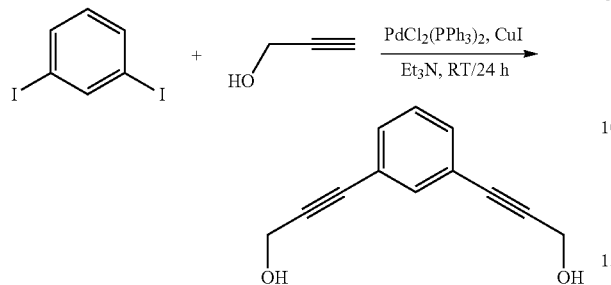

To an oven dried 2 L 3-neck round bottom flask attached to a mechanical stirrer was added 1,3-diiodobenzene (36.0 g; 109.1 mmol) to 225 mL of dry triethylamine under nitrogen. To the light brown solution was added bis(triphenylphosphine)palladium(II) dichloride (4.2 g; 6.0 mmol, 0.05 mol %) followed by copper (I) iodide (0.33 g; 1.74 mmol, 0.015 mol %). The dark green mixture was stirred for 5 minutes. Propargyl alcohol (21.5 mL; 371.2 mmol) was added dropwise via an addition funnel. A slight exotherm was noticed after the addition. The dark brown mixture was stirred for 3 hours at room temperature. TLC (5% ethyl acetate/hexane UV detection) indicated no starting material remained. The reaction was stirred overnight, 1,500 mL of ethyl acetate was added and it was stirred for an additional 24 hours. The reaction mixture was filtered and the filtrate was concentrated in vacuo to recover 30.4 g of a brown oil. The crude product was purified on silica gel using a continuous gradient of 40-100% ethyl acetate/hexane to recover 15.0 g (74%) of desired product. $^1$H NMR 400 MHz (CDCl$_3$) δ 7.51 (1H), 7.40, (1H), 7.38 (1H), 7.29 (1H), 4.50-4.49 (d, 4H), 1.71-1.68 (2H). $^{13}$C NMR 100 MHz (CDCl$_3$) δ 134.6, 131.6, 128.4, 122.8, 87.9, 84.7 and 51.4.

Preparation of 3,3'-(1,3-phenylene)bis(propan-1-ol)

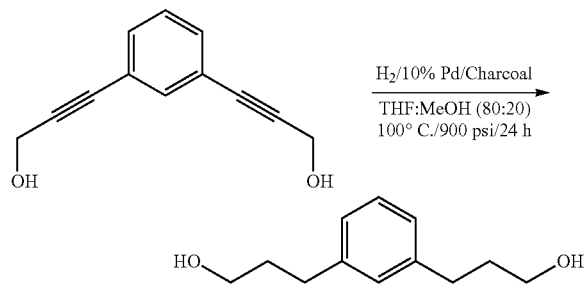

3,3'-(1,3-phenylene)bis(prop-2-yn-1-ol)(2.0 g; 10.7 mmol) was dissolved in 11 mL of anhydrous methanol and placed in a Teflon lined autoclave. A slurry of palladium on charcoal (0.4 g; 10% palladium on charcoal) in 40 mL of dry THF was added to the liner over a blanket of nitrogen. The autoclave was closed and pressurized with H$_2$. After 24 hours the reaction solution was filtered through a pad of Celite. The filtrate was concentrated in vacuo to recover 2.1 g (100%) of crude desired product. This product was taken forward without purification. $^1$H NMR 400 MHz (CDCl$_3$) δ 7.22-7.18 (1H), 7.04 (1H), 7.02 (2H), 3.69-3.64 (4H), 2.70- 2.63 (4H), 1.92-1.85 (4H) 1.51-1.49 (2H). $^{13}$C NMR 100 MHz (CDCl$_3$) δ 141.9, 128.6, 128.4, 125.9, 62.3, 34.2, and 32.0.

Preparation of 1,3-phenylenebis(propane-3,1-diyl) bis(4-methylbenzenesulfonate)

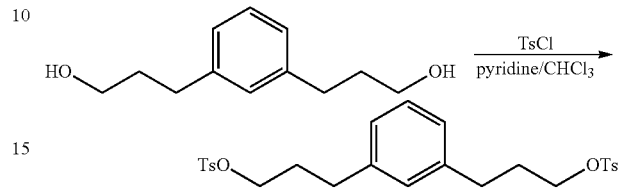

In a dry 25 mL vial with a septum was added 3,3'-(1,3-phenylene)bis(propan-1-ol) (0.2 g; 1.0 mmol) dissolved in 2.0 mL of anhydrous chloroform at room temperature under nitrogen. Pyridine (0.17 mL; 2.1 mmol) was added and the solution was cooled to 0° C. (ice-bath). p-toluenesulfonyl chloride (0.43 g; 2.2 mmol) was added and the light orange solution was allowed to warm to room temperature. After 24 hours the reaction was diluted with 10 mL of 5% HCl and the layers were separated. The organic layer was washed with 10 mL of brine and pre-adsorbed onto silica. The crude product was purified on silica using a continuous gradient of 0 to 100% ethyl acetate/hexane to recover 0.28 g (55%) of the desired compound. $^1$H NMR 400 MHz (CDCl$_3$) δ 7.79-7.77 (4H), 7.35-7.33 (4H), 7.11 (1H), 6.90-6.85 (3H), 4.03-4.00 (4H), 2.61-2.58 (4H), 2.45 (6H), 1.94-1.91 (4H). $^{13}$C NMR 100 MHz (CDCl$_3$) δ 144.7, 140.6, 133.1, 129.8, 128.6, 127.9, 126.2, 69.6, 31.4, 30.4 and 21.6.

Preparation of 1,1'-(1,3-phenylenebis(propane-3,1-diyl))bis(1-methylpyrrolidin-1-ium) 4-methylbenzenesulfonate

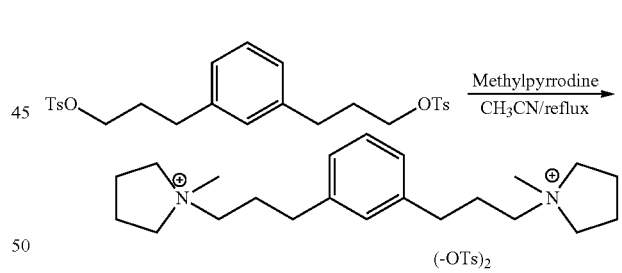

In a dry 20 mL vial with a relief cap and stir bar was added 1.0 g (1.9 mmol) of the 1,3-phenylenebis(propane-3,1-diyl) bis(4-methylbenzenesulfonate) under nitrogen. 2 mL of dry acetonitrile was added and the pale yellow solution was stirred for 5 minutes. Methylpyrrolidine (0.64 mL; 6.0 mmol) was added dropwise and the solution was stirred at room temperature for one hour. TLC (2:1 hexane:ethyl acetate, UV detection) indicated that starting material remained. The solution was heated to 80° C. After one hour TLC indicated the starting material was consumed. The reaction was cooled to room temperature and stored overnight. The reaction solution was concentrated in vacuo at 45° C. to recover 1.2 g (96%) of the desired product. $^1$H NMR 400 MHz (CD$_3$CN) δ 7.64-7.62 (4H), 7.26-7.23 (2H), 7.18 (4H), 7.11-7.09 (2H), 3.45-3.34 (8H), 3.33-3.31 (4H), 2.95 (6H), 2.64-2.58 (4H), 2.34 (6H), 2.08-2.04 (12H). $^{13}$C NMR 100 MHz (CD$_3$CN) δ 145.4, 140.4, 138.3, 128.3, 128.2, 128.0, 126.0, 125.3, 117.0, 63.7, 63.0, 47.5, 31.4, 24.7, 23.3, 20.8 and 19.9.

Preparation of 1,1'-(1,3-phenylenebis(propane-3,1-diyl))bis(1-methylpyrrolidin-1-ium) hydroxide

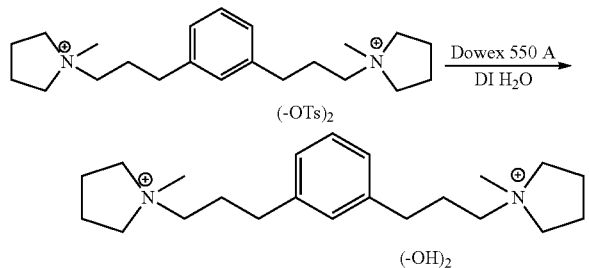

545 g of Dowex Monosphere 550A resin was placed into a 500 mL Nalgene screw cap bottle. The resin was rinsed 3×500 mL with deionized water to remove any fines. 27.3 g (40.5 mmol) of the 1,1'-(1,3-phenylenebis(propane-3,1-diyl))bis(1-methylpyrrolidin-1-ium) 4-methylbenzenesulfonate was dissolved in 100 mL of deionized water and added to the Nalgene container. Deionized water was added to the container until 80% filled. The top of the container was closed and taped. The container was placed on a mechanical roller overnight to facilitate the anion exchange. The slurry was filtered through a Buchner funnel and rinsed with deionized water until pH 9. The aqueous solution was concentrated in vacuo at 40° C. to the desired concentration to afford the dihydroxide. $^1$H NMR 400 MHz (D$_2$O) δ7.22-7.18 (1H), 7.04-7.03 (3H), 3.34-3.18 (7H), 3.17-3.14 (4H), 2.84 (6H), 2.57-2.54 (4H), 2.18-1.92 (12H). $^{13}$C NMR 100 MHz (D$_2$O) δ 140.9, 129.0, 128.5, 126.5, 64.2, 63.4, 47.9, 31.5, 24.7 and 21.1.

A suitable synthesis regimen for the compound of formula II from 1,4-bis(chloromethyl)benzene is described below.

Preparation of tetraethyl 2,2'-(1,4-phenylenebis(methylene))dimalonate

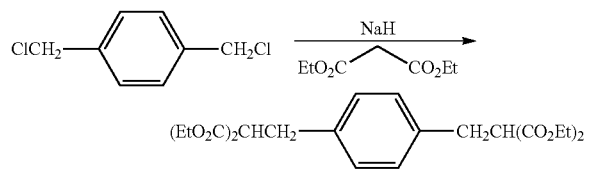

An oven dried 1 L 3-necked jacketed flask equipped with mechanical stirrer was assembled hot and cooled under flowing N$_2$ then charged with 29.6 g 60% sodium hydride in mineral oil. The contents were cooled to −5° C. with circulating glycol-water and 400 mL anhydrous DMF added via cannula. 150 mL (1 mole) diethylmalonate was added dropwise to the flask over 40 minutes and then the contents were warmed to 35° C. After one hour, all the NaH had dissolved and the solution was clear. To this was added 40 g (228 mmol) 1,4-bis(chloromethyl)benzene all at once. The temperature rose to 68° C. and a solid formed. After heating with steam for 30 min, the flask was cooled to 15° C. and a solution of 20 mL concentrated HCl in 400 mL H$_2$O was added. The contents of the flask was then transferred to a separatory funnel, where the viscous lower layer was withdrawn as product. After removing volatiles on a rotary evaporator, the product was distilled at 80° C. @ 190 mTorr to give 94.3 g (98%) of the desired liquid product. The NMR shows a trace of diethylmalonate. The product had the expected $^{13}$C NMR and $^1$H NMR spectra. $^{13}$C NMR (CDCl$_3$): δ 168.7(C$_q$), 128.8(CH), 136.4(C$_q$), 61.3(CH$_2$), 53.7(CH), 34.1(CH$_2$), 13.9(CH$_3$) $^1$H NMR(CDCl$_3$): δ 7.07 (s,3.9H), 3.56(t, 2.1H), 3.12(d, 3.9H).

Preparation of 3,3'-(1,4-phenylene)dipropanoic acid

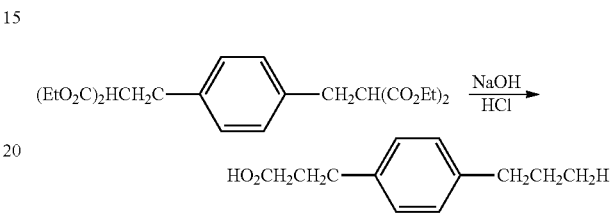

94.3 g of tetraethyl 2,2'-(1,4-phenylenebis(methylene)) dimalonate was heated at reflux for 90 min with 300 mL H$_2$O, 50 mL ethanol, and 50.3 g (1250 mmol) NaOH. The ethanol was removed on a rotary evaporator to leave 320 g residue. The residue was extracted with 100 mL pentane to remove the mineral oil left from the sodium hydride (2.1 g oil obtained from evaporated pentane). The aqueous solution was acidified to pH 1.5 with 63 g (642 mmol) H$_2$SO$_4$ added dropwise over 20 minutes. The temperature rose to 62° C. A bubbler was attached to visualize CO$_2$ evolution and the mixture heated at reflux until all gas evolution ceased (refluxed 48 hours but only observed gas evolution for first 6 hours). The product was filtered and dried to constant weight at 80° C. to give 43.8 g (101%) product. The product had the expected $^{13}$C NMR and $^1$H NMR spectra. $^{13}$C NMR(D$_2$O+NaOH): δ 182.5(C$_q$), 139.7(C$_q$), 128.4(CH), 39.4(CH$_2$), 31.5(CH$_2$). $^1$H NMR(D$_2$O+NaOH): δ 7.12 (s, 3.9H), 2.78(t, 4.1H), 2.40(t, 3.9H).

Preparation of diethyl 3,3'-(1,4-phenylene)dipropanoate

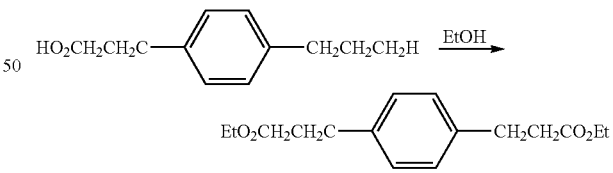

To 153 g of 3,3'-(1,4-phenylene)dipropanoic acid was added 800 mL USP ethanol and 5 mL concentrated H$_2$SO$_4$, and the mixture heated at reflux for 2 hours, cooled, quenched with 14 g K$_2$CO$_3$ in 30 mL H$_2$O and set in a refrigerator at 0° C. After crystallizing overnight, the solid was filtered and dried to constant weight at 55° C. over 2 weeks. Samples taken at intermediate times indicated residual H$_2$O. The solid obtained 134.8 g (70%) was free of water by NMR. GCMS showed the product with the expected m/z=278 and a trace component with long retention time with m/z=277 thought to be a trace of triester from incompletely decarboxylated tetra-acid. The product had the expected $^{13}$C NMR and $^1$H NMR spectra. $^{13}$C NMR (CDCl$_3$): δ 172.0(C$_q$), 138.5(C$_q$), 128.4(CH), 60.4(CH$_2$), 35.9(CH$_2$), 30.5(CH$_2$), 14.2(CH$_3$). $^1$H NMR(CDCl$_3$): δ 7.13 (s, 4.5H), 4.13(q, 3.8H), 2.92(t, 4.2H), 2.60(t, 3.8H), 1.25(t, 5.6H).

Preparation of 3,3'-(1,4-phenylene)bis(propan-1-ol)

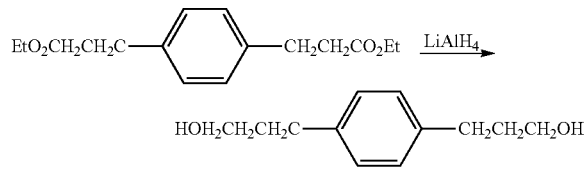

In a 2 L 3-necked jacketed, oven-dried flask equipped with mechanical stirrer, equalizing dropping funnel and reflux condenser, assembled hot and cooled under N$_2$ were added 300 mL anhydrous THF and 8.4 g (221 mmol) LiAlH$_4$ pellets. After brief stirring, 49.7 g (179 mmol) of diethyl 3,3'-(1,4-phenylene)dipropanoate in 100 mL THF was dripped in over 30 min followed by 50 mL anhydrous THF to wash the funnel. The mixture became warm and considerable solid formed. The mixture was heated at reflux for 20 minutes, cooled and let stand overnight when it was quenched by dropwise addition of 42 mL H$_2$O+42 mL THF, then 12 g NaOH in 120 g H$_2$O. The supernatant was decanted through fluted filter paper, the solid washed with 100 mL Et$_2$O and the volatiles removed on a rotary evaporator to a bath temperature of 85° C. The residue was then distilled at 110° C. at 250 mTorr to give 33.9 g (97%) product. The product had the expected $^{13}$C NMR and $^1$H NMR spectra. $^{13}$C NMR(CDCl$_3$): δ 139.3(C$_q$), 128.4(CH), 62.0(CH$_2$), 34.2(CH$_2$), 31.6(CH$_2$). $^1$H NMR(CDCl$_3$): δ 7.12 (s, 3.9H), 3.65(q, 3.9H), 2.97(t, 2.3H), 1.88(m, 4.0H).

Preparation of 1,4-phenylenebis(propane-3,1-diyl) bis(4-methylbenzenesulfonate)

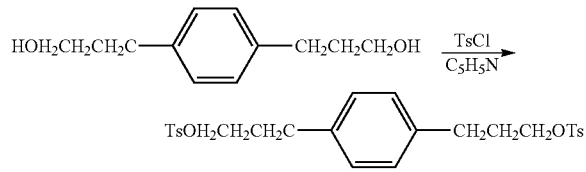

92.8 g (478 mmol) of 3,3'-(1,4-phenylene)bis(propan-1-ol), 275 mL CHCl$_3$ (amylene stabilized), and 63 mL pyridine were placed in a jacketed flask and cooled to 0° C. while stirring magnetically. To this was added 190 g (1000 mmol) p-toluenesulfonyl chloride in spoonfuls over 10 min. The temperature rose to 34° C. The mixture was stirred 1 hour then poured into 655 mL H$_2$O+140 mL concentrated HCl, resultant pH<1. The lower, viscous layer was drawn off and washed 1×250 mL saturated NaCl. The resulting oil set to a solid mass which was broken up and dried to constant weight (3 hours) at 60° C. @ 1 mTorr to give 219 g (91%) material of acceptable purity by $^{13}$C NMR.

Preparation of 1,4-bis(3-(pyrrolidin-1-yl)propyl)benzene

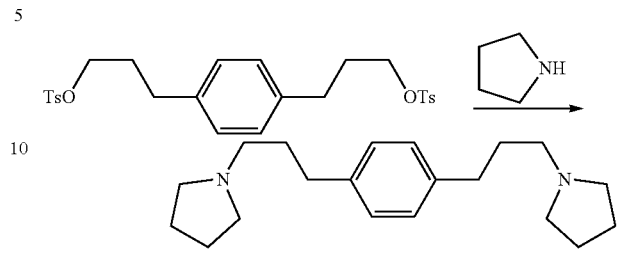

146 g (291 mmol) of 1,4-phenylenebis(propane-3,1-diyl) bis(4-methylbenzenesulfonate) was dissolved in 440 mL warm CHCl$_3$ (amylene stabilized) and 141 g (1.99 mol) pyrrolidine was added all at once. On warming, there was a gentle exotherm. The mixture was left at reflux overnight during which time it turned black. It was cooled to 0° C. and poured onto 80 g NaOH in 800 mL H$_2$O, 400 mL H$_2$O and 200 mL diethylether added and the lower, very dark layer drawn off. 300 mL H$_2$O was added to the remaining mixture and again the lower layer was withdrawn. The combined lower layers were reduced on a rotary evaporator at 95° C. @ 50 mBar and the black oil distilled at 200° C. @ 140 mTorr to give 82.8 g (95%) yellow oil that gradually solidified on standing. GCMS of the product showed the expected molecular m/z=300 and about 3% of a product (m/z=225) identified as 1-tosylpyrrolidine from the GCMS library at 97% confidence. The product had the expected $^{13}$C NMR and $^1$H NMR spectra. $^{13}$C NMR(CDCl$_3$): δ 139.5(C$_q$), 128.2(CH), 56.0(CH$_2$), 54.1(CH$_2$), 33.5(CH$_2$), 30.7(CH$_2$), 23.4(CH$_2$). $^1$H NMR(CDCl$_3$): δ 7.04(s, 4.2H), 2.57(t, 4.3H), 2.43(m, 11H), 1.80-1.71(m, 12.5H).

Preparation of 1,1'-(1,4-phenylenebis(propane-3,1-diyl))bis(1-methylpyrrolidin-1-ium) hydroxide

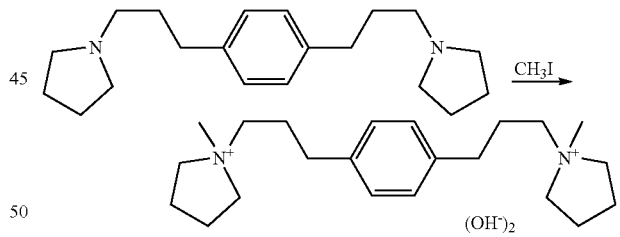

To 41.4 g (138 mmol) of 1,4-bis(3-(pyrrolidin-1-yl)propyl)benzene in 150 mL acetone in a 500 mL Erlenmeyer was added 41 mL (99 g, 699 mmol) iodomethane in portions over 15 min. The solution warmed almost to reflux and solid precipitated. The flask was stoppered, wrapped in Al foil, and allowed to stand at room temperature for 48 hours, filtered, washed with 100 mL diethylether and dried to constant weight at 60° C. to give 65.2 g (80%). This material was ion exchanged using the batch method described previously to give 163 g of solution. Titration of 2.13 g of this solution diluted to 25 mL took 7.41 mL to titrate 83.0 mg potassium hydrogen phthalate. This calculates for 11.7% as the dihydroxide. Integration of the exchanged solution comparing the organic hydrogen to water signal gave 12.0% as the dihydroxide. The product had the expected $^{13}$C NMR, $^1$H NMR, and $^{14}$N NMR spectra. $^{13}$C NMR(D$_2$O): δ 139.6(C$_q$), 128.9(CH), 64.4(CH$_2$), 63.6(CH$_2$), 48.3(CH$_3$), 31.3(CH$_2$), 24.9(CH$_2$), 21.4(CH$_2$). $^1$H NMR(D$_2$O): δ 7.25(s, 4.0H), 3.43(m, 8.3H), 3.29(m, 4.0H), 2.97(s, 5.9H), 2.68(t,3.9H), 2.17(m,12.0H). $^{14}$N NMR(D$_2$O): δ 57.8(⊗v$_{1/2}$=14 Hz, calculated shift 54.0 ppm).

In a modification of the above synthesis regimen for the dication of formula II, 1,4-phenylenebis(propane-3,1-diyl) bis(4-methylbenzenesulfonate) is reacted with 1-methylpyrrolidine in chloroform or acetonitrile to produce the dication directly without intermediate production of the diamine.

A person of ordinary skill in the art would understand that similar reactions can be used to produce the 1,1'-(1,2-phenylenebis(propane-3,1-diyl))bis(1-methylpyrrolidin-1-ium) dication of formula III from 1,2-bis(halomethyl)benzenes.

Likewise, a person of ordinary skill in the art would understand that similar reactions can be used to produce the 1,1'-(1,4-phenylenebis(propane-3,1-diyl))bis(1-methylpyrrolidin-1-ium) dication of formula II from 1,4-dihalobenzenes.

Likewise, a person of ordinary skill in the art would understand that similar reactions to those described above can be used to produce the 1,1'-(1,2-phenylenebis(propane-3,1-diyl))bis(1-methylpyrrolidin-1-ium) dication of formula III from 1,2-dihalobenzenes.

Synthesis of EMM-28

Example 1

A synthesis gel was prepared using Ludox LS30 as the silicon source, fumed alumina as the aluminum source and the dication of formula I (meta) as the organic structure directing agent, Q. The synthesis gel had molar ratios of H$_2$O/SiO$_2$=30, OH$^-$/SiO$_2$=0.30, Q/SiO$_2$=0.15 and Si/Al (atomic ratio)=500.

The preparation and crystallization of the synthesis gel was conducted according to the following procedure. 9.6 g of the organic structure directing agent was mixed with 0.5 g of distilled water and then 2.26 mg of fumed alumina was added to the mixture, followed by 4.4 g of Ludox LS30 and 13.35 mg of EMM-28 seeds. The mixture was stirred continuously during all the additions and then stirred for an additional hour, after which the mixture was poured into a Teflon lined 23 ml Parr reactor. The reactor was then heated in a tumbling oven at 160° C. for 14 days.

The resulting product was analyzed by powder XRD and, as shown in Table 3, was found to be EMM-28 with minor amount of amorphous (AMO) impurity.

Examples 2 to 4

The process of Example 1 was repeated at various Si/Al values between 50 and 1000 and the results are shown in Table 3.

Example 5

The process of Example 1 was repeated but with the molar ratio of H$_2$O/SiO$_2$=50. The resulting product was analyzed by powder XRD and found to be substantially amorphous (Table 3).

Examples 6 and 7

The process of Example 1 was repeated using Ultrasil as the silicon source at Si/Al values of 100 and 500. As shown in Table 3, at the Si/Al value of 100, powder XRD revealed the product to be EMM-28 with a minor amount of amorphous (AMO) impurity, whereas at the Si/Al value of 500, the product was found to be substantially amorphous.

Example 8

The process of Example 1 was repeated, again using Ludox LS30 as the silicon source, but with Q/SiO$_2$=0.1, H$_2$O/SiO$_2$=25, OH$^-$/SiO$_2$=0.20 and 1 wt % of EMM-28 seeds (based on silica). The resulting product was analyzed by powder XRD and, as shown in Table 3, was found to be EMM-28. The XRD pattern of the as-synthesized material of Example 8 is shown in FIG. 1 (upper pattern).

Example 9

The process of Example 1 was repeated, again using Ludox LS30 as the silicon source, but with Q/SiO$_2$=0.05, H$_2$O/SiO$_2$=25, OH$^-$/SiO$_2$=0.10 and 1 wt % of EMM-28 seeds (based on silica). The resulting product was analyzed by powder XRD and, as shown in Table 3, was found to be EU-1. The XRD pattern of the as-synthesized material of Example 9 is shown in FIG. 1 (lower pattern).

Examples 10 to 13

The process of Example 1 was repeated but using Al(NO$_3$)$_3$.9H$_2$O as the aluminum source and with the Si/Al values being 1,000 (Example 10), 100 (Example 11) and 500 (Examples 12 and 13). In the case of Examples 10 to 12, the reaction mixture included the same seed addition as used in Example 1, whereas in Example 13 seeds were omitted. As shown in Table 3, powder XRD analysis showed the products of Examples 10 and 13 to EMM-28 and the products of Examples 11 and 12 to be EU-1.

Example 14

The seedless preparation of Example 13 was repeated but with the Al(NO$_3$)$_3$.9H$_2$O being replaced by MS-25 silica-alumina supplied by W.R. Grace & Co. Powder XRD analysis showed the product to be EMM-28 with a small amount of an impurity phase.

Example 15

Figure 2:
FIG. 2 shows scanning electron micrograph (SEM) images of the EMM-28 product of Example 15 at different magnifications.

A synthesis gel having the composition given in Table 3 was prepared by initially mixing 49.76 g of the dication of formula I (meta) as the organic structure directing agent, Q, with 2.838 g of water. To the resultant mixture were added 0.054 g MS-25 silica-alumina, 19.041 g of Ludox LS30 silica and 0.132 g of EMM-28 seeds. The mixture was stirred continuously during all the additions and then stirred for an additional hour, after which the mixture was poured into a 60 ml stirred autoclave liner. The liner was then heated in a tumbling oven at 160° C. for 7 days. Powder XRD analysis showed the product to be EMM-28 (Table 3). Scanning electron micrograph (SEM) images of the product are shown in FIG. 2.

TABLE 3

| Ex. | Si Source | Al Source | Seeds (Y/N) | Si/Al | $H_2O$/Si | $OH^-$/Si | Product |
|---|---|---|---|---|---|---|---|
| 1 | Ludox LS30 | Fumed $Al_2O_3$ | Y | 500 | 30 | 0.30 | EMM-28 (slight AMO) |
| 2 | Ludox LS30 | Fumed $Al_2O_3$ | Y | 50 | 30 | 0.30 | AMO |
| 3 | Ludox LS30 | Fumed $Al_2O_3$ | Y | 100 | 30 | 0.30 | AMO |
| 4 | Ludox LS30 | Fumed $Al_2O_3$ | Y | 1000 | 30 | 0.30 | EMM-28 (slight AMO) |
| 5 | Ludox LS30 | Fumed $Al_2O_3$ | Y | 500 | 50 | 0.30 | AMO |
| 6 | Ultrasil | Fumed $Al_2O_3$ | Y | 100 | 30 | 0.30 | EMM-28 (slight AMO) |
| 7 | Ultrasil | Fumed $Al_2O_3$ | Y | 500 | 30 | 0.30 | AMO |
| 8 | Ludox LS30 | Fumed $Al_2O_3$ | Y | 500 | 25 | 0.20 | EMM-28 |
| 9 | Ludox LS30 | Fumed $Al_2O_3$ | Y | 500 | 25 | 0.10 | EU-1 |
| 10 | Ludox LS30 | $Al(NO_3)_3 \cdot 9H_2O$ | Y | 1000 | 30 | 0.30 | EMM-28 |
| 11 | Ludox LS30 | $Al(NO_3)_3 \cdot 9H_2O$ | Y | 100 | 30 | 0.30 | EU-1 |
| 12 | Ludox LS30 | $Al(NO_3)_3 \cdot 9H_2O$ | Y | 500 | 30 | 0.30 | EU-1 |
| 13 | Ludox LS30 | $Al(NO_3)_3 \cdot 9H_2O$ | N | 500 | 30 | 0.30 | EMM-28 |
| 14 | Ludox LS30 | MS-25 | N | 500 | 30 | 0.30 | EMM-28 (small impurity) |
| 15 | Ludox LS30 | MS-25 | Y | 500 | 30 | 0.30 | EMM-28 |

Example 16

The process of Example 1 was repeated but using $Al(NO_3)_3 \cdot 9H_2O$ as the aluminum source and the dication of formula II (para) as the organic structure directing agent, Q. The resulting product was analyzed by powder XRD and found to be MCM-22.

Example 17

The process of Example 16 was repeated but using a mixture of the dication of formula I (meta) and the dication of formula II (para), in a 60 to 40 weight ratio, as the organic structure directing agent, Q. In this case, powder XRD analysis found the product to be EMM-28 with some impurity phase.

Example 18

The process of Example 17 (mixed meta/para directing agent) was repeated but with the seeds omitted. Powder XRD analysis found the product to be an unknown crystalline phase.

Example 19

The process of Example 1 was repeated but using $Al(NO_3)_3 \cdot 9H_2O$ as the aluminum source and a dication of formula III (ortho) as the organic structure directing agent, Q. Powder XRD analysis found the product to be RUB-35. The same result was obtained when the Ultrasil, rather than Ludox LS30, was used as the silica source.

Example 20

The process of Example 19 was repeated but with the organic structure directing agent, Q, being a 50 to 50 weight ratio mixture of the dication of formula III (ortho) and the dication of formula II (para). Powder XRD analysis showed the product to be a mixture of EU-1 and ZSM-12. When the seeds were omitted, the product was found to be ZSM-12 alone.

Example 21

A synthesis gel without added aluminum and with molar ratios of $H_2O/SiO_2=32$, $OH^-/SiO_2=0.4$ and $Q/SiO_2=0.2$ was prepared using tetramethyl orthosilicate (TMOS) as a first silicon source, trimethoxyphenylsilane (MePhSi) as a second silicon source and the dication of formula I (meta) as the organic structure directing agent, Q.

The preparation and crystallization of the synthesis gel was conducted according to the following procedure. 0.61 mL of MePhSi was mixed with 2.42 mL TMOS and to the mixture was added 11.62 mL of the organic structure directing agent and 0.012 g of EMM-28 seeds. The mixture was stirred continuously during all the additions and then stirred for an additional 10 minutes, after which the mixture was placed in a freeze dryer to remove all water. After removing the mixture from the freeze dryer, 11.7 mL of distilled water was back-added and the mixture was stirred. The mixture was then transferred to a 23 mL Parr reactor and heated in a tumbling oven at 160° C. for 5 days. The resulting product was analyzed by powder XRD and found to be EMM-28.

Example 22

The process of Example 21 was repeated but with the seeds omitted. Powder XRD analysis found the product to be EMM-28 together with an unknown crystalline phase.

Examples 23 and 24

The process of Example 21 was repeated but with the crystallization temperature at 180° C. both with seeds in the synthesis mixture (Example 23) and with the seeds omitted (Example 24). The resulting products were analyzed by powder XRD and were found to be EMM-28 in the case of the seeded synthesis and ZSM-12 in the case of the unseeded synthesis.

Example 25

The process of Example 22 (no seeds) was repeated but with the crystallization temperature at 170° C. The resulting product was analyzed by powder XRD and found to be amorphous.

Example 26

The process of Example 21 (with seeds) was repeated but with the crystallization temperature at 200° C. The resulting product was analyzed by powder XRD and found to be cristobalite.

Additionally or alternatively, the invention can include one or more of the following embodiments.

Embodiment 1. A synthetic crystalline material having, in its as-calcined form, an X-ray diffraction pattern including the following peaks:

| d-spacing (Å) | Relative Intensity (I/Io × 100) |
|---|---|
| 19.85 ± 0.30 | W |
| 11.20 ± 0.30 | VS |
| 9.97 ± 0.20 | W |
| 8.80 ± 0.10 | M |
| 6.86 ± 0.10 | W |
| 6.49 ± 0.10 | VW |
| 5.85 ± 0.10 | VW |
| 5.70 ± 0.10 | VW |
| 5.61 ± 0.10 | VW |
| 5.12 ± 0.10 | VW |
| 4.60 ± 0.05 | VW |
| 4.45 ± 0.05 | VW |
| 4.33 ± 0.05 | M-S |
| 4.25 ± 0.05 | VW-W |
| 4.15 ± 0.05 | VW-W |
| 4.06 ± 0.05 | VW |
| 3.98 ± 0.05 | VW |
| 3.88 ± 0.05 | VW |
| 3.76 ± 0.05 | VW-W |
| 3.73 ± 0.05 | VW-W |
| 3.68 ± 0.05 | W |
| 3.53 ± 0.05 | W |
| 3.43 ± 0.05 | W |
| 3.28 ± 0.05 | W-M |
| 3.19 ± 0.05 | VW |
| 3.16 ± 0.05 | VW |
| 3.11 ± 0.05 | VW |
| 3.07 ± 0.05 | VW |
| 2.94 ± 0.025 | VW |
| 2.79 ± 0.025 | VW |
| 2.60 ± 0.025 | VW |
| 2.53 ± 0.025 | VW |
| 2.50 ± 0.025 | VW |
| 2.46 ± 0.025 | VW |
| 2.41 ± 0.025 | VW |
| 2.34 ± 0.025 | VW | wherein the material optionally has a composition comprising the molar relationship $(n)X_2O_3:YO_2$, wherein n is a number less than 0.05, X is a trivalent element, and Y is a tetravalent element; optionally wherein X includes one or more of B, Al, Fe, and Ga (e.g., including at least Al); optionally wherein Y includes one or more of Si, Ge, Sn, Ti, and Zr (e.g., including at least Si and/or Ge).

Embodiment 2. A synthetic crystalline material having, in its as-synthesized form, an X-ray diffraction pattern including the following peaks:

| d-spacing (Å) | Relative Intensity (I/Io × 100) |
|---|---|
| 20.00 ± 0.30 | W |
| 11.56 ± 0.30 | VS |
| 10.03 ± 0.20 | W |
| 8.87 ± 0.20 | W-M |
| 6.91 ± 0.10 | W |
| 6.66 ± 0.10 | VW |
| 6.03 ± 0.10 | VW |
| 5.70 ± 0.10 | VW |
| 5.55 ± 0.10 | VW |
| 5.14 ± 0.10 | W-M |
| 4.64 ± 0.05 | W |
| 4.43 ± 0.05 | VS |
| 4.36 ± 0.05 | S-VS |
| 4.28 ± 0.05 | W-M |
| 4.16 ± 0.05 | M |
| 4.00 ± 0.05 | VW |
| 3.93 ± 0.05 | W |
| 3.84 ± 0.05 | M |
| 3.77 ± 0.05 | M |
| 3.70 ± 0.05 | M |
| 3.54 ± 0.05 | VW |
| 3.45 ± 0.05 | M |
| 3.31 ± 0.05 | M-S |
| 3.25 ± 0.05 | VW-W |
| 3.17 ± 0.05 | VW |
| 3.12 ± 0.05 | VW |
| 3.00 ± 0.05 | VW |
| 2.96 ± 0.025 | VW |
| 2.84 ± 0.025 | VW |
| 2.79 ± 0.025 | VW |
| 2.76 ± 0.025 | VW |
| 2.63 ± 0.025 | VW |
| 2.57 ± 0.025 | VW |
| 2.47 ± 0.025 | VW |
| 2.36 ± 0.025 | VW |
| 2.34 ± 0.025 | VW | wherein the material optionally has a composition comprising the molar relationship $(m)M:(b)Q:(n)X_2O_3:YO_2:(z)H_2O$, wherein m is a number having a value equal to or greater than 0 to less than or equal to 0.1, b is a number having a value greater than 0 to less than or equal to 0.05, n is a number less than 0.025, z is a number having a value greater than or equal to 0 to less than or equal to 0.2, M is an alkali metal cation, X is a trivalent element optionally including one or more of B, Al, Fe, and Ga (e.g., including at least Al); Y is a tetravalent element optionally including one or more of Si, Ge, Sn, Ti, and Zr (e.g., including at least Si and/or Ge), and Q is an organic structure directing agent selected from one or more of the dications of formula I and II:

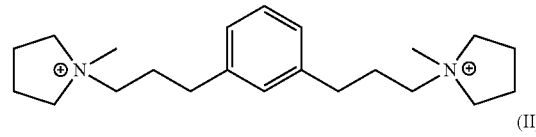

(I)

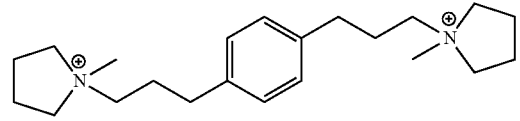

(II)

Embodiment 3. The material of embodiment 2, wherein the material has a composition comprising the molar relationship $(k)F:(b)Q:(n)X_2O_3:YO_2:(z)H_2O$, wherein k is a number having a value equal to or greater than 0 to less than or equal to 0.01, b is a number having a value greater than 0 to less than or equal to 0.05, n is a number less than 0.025, z is a number having a value greater than or equal to 0 to less than or equal to 0.2, F is a fluoride ion, X is a trivalent element optionally including one or more of B, Al, Fe, and Ga (e.g., including at least Al); Y is a tetravalent element optionally including one or more of Si, Ge, Sn, Ti, and Zr (e.g., including at least Si and/or Ge), and Q is an organic structure directing agent, e.g., selected from one or more of the dications of formula I and II.

Embodiment 4. A process for producing the synthetic crystalline material of any one of the preceding embodiments, the process comprising the steps of:

(i) preparing a synthesis mixture capable of forming said material, said mixture comprising water, a source of hydroxyl ions, a source of an oxide of a tetravalent element Y, a source of a trivalent element X, and an organic structure directing agent (Q) selected from one or more of the dications of formula I and II:

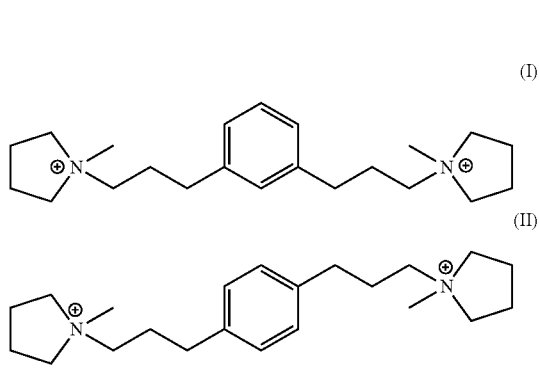

wherein the mixture optionally has a composition, in terms of mole ratios, within the following ranges: $X_2O_3/YO_2$ from 0 to about 0.05; $H_2O/YO_2$ from about 2 to about 100; $OH^-/YO_2$ from about 0.05 to about 0.6; and $Q/YO_2$ from about 0.04 to about 0.30, the mixture optionally further comprising a source of seeds;

(ii) heating the mixture under crystallization conditions including a temperature of from about 100° C. to about 200° C. until crystals of said material are formed;

(iii) recovering the crystalline material from step (ii); and (iv) optionally treating the crystals recovered in (iii) to remove at least part of the organic structure directing agent (Q).

Embodiment 5. A synthetic porous crystalline material produced by the process of embodiment 4.

Embodiment 6. A process for converting a feedstock comprising an organic compound to a conversion product, the process comprising the steps of:

(i) contacting said feedstock with a catalyst, at organic compound conversion conditions, to produce an effluent containing converted product, said catalyst comprising an active form of the synthetic porous crystalline material of embodiment 1 or embodiment 5; and (ii) recovering converted product from the effluent.

Embodiment 7. A process for selectively separating one or more desired components of a feedstock from remaining components of the feedstock, the process comprising the steps of:

(i) contacting said feedstock with a sorbent, at effective sorption conditions, said sorbent comprising an active form of the synthetic porous crystalline material of embodiment 1 or embodiment 5, thereby forming a sorbed product and an effluent product; and (ii) recovering the one or more desired components (e.g., comprising, consisting essentially of, or being $CO_2$, $H_2S$, $NH_3$, $SO_3$, an aliphatic hydrocarbon such as $CH_4$, an aromatic hydrocarbon such as a single-ring aromatic hydrocarbon, and/or an olefin such as ethylene, propylene, butene, pentene, hexane, or the like, or any combination thereof) from either the sorbed product or the effluent product.

Embodiment 8. A synthetic porous crystalline material having within its pore structure a dication of formula I or II:

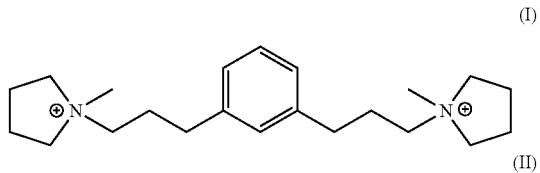

Embodiment 9. An organic nitrogen compound comprising a dication of formula I, II and III:

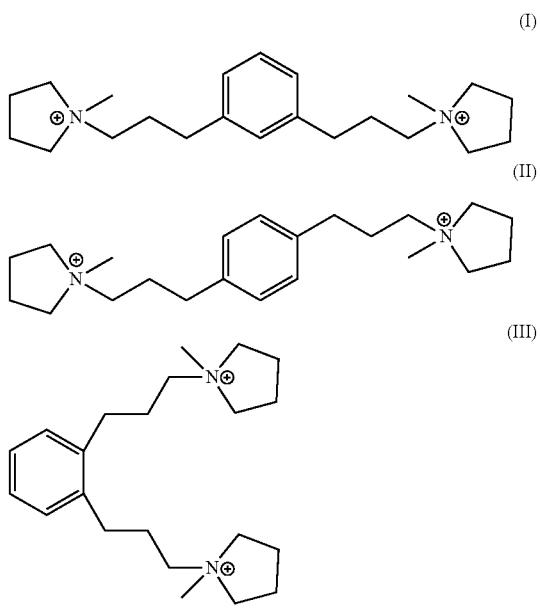

Embodiment 10. A method of producing a 1,1'-(1,x-phenylenebis(propane-3,1-diyl))bis(1-methylpyrrolidin-1-ium) compound, where x is 2, 3 or 4, the method comprising:

reacting 1,x-bis(halomethyl)benzene with a dialkyl malonate to produce a tetraalkyl 2,2'-(1,x-phenylenebis(methylene))dimalonate;

converting at least part of the tetraalkyl 2,2'-(1,x-phenylenebis(methylene))dimalonate to 3,3'-(1,x-phenylene)dipropanoic acid;

reducing at least part of the 3,3'-(1,x-phenylene)dipropanoic acid, or an ester thereof, to 3,3'-(1,x-phenylene)bis(propan-1-ol));

reacting at least part of the 3,3'-(1,x-phenylene)bis(propan-1-ol)) with an alkyl- or aryl-sulfonyl halide (e.g., p-toluenesulfonyl chloride) to produce the corresponding sulfonate diester;

reacting at least part of the sulfonate diester with pyrrolidine to produce 1,x-bis(3-(pyrrolidin-1-yl)propyl)benzene; and reacting at least part of the 1,x-bis(3-(pyrrolidin-1-yl)propyl)benzene with a methyl halide to produce a 1,1'-(1,x-phenylenebis(propane-3,1-diyl))bis(1-methylpyrrolidin-1-ium) halide.

Embodiment 11. A method of producing a 1,1'-(1,x-phenylenebis(propane-3,1-diyl))bis(1-methylpyrrolidin-1-ium) compound, where x is 2, 3 or 4, the method comprising:

reacting at least part of the sulfonate diester of 3,3'-(1,x-phenylene)bis(propan-1-ol)) from embodiment 10 with 1-methylpyrrolidine to produce a 1,1'-(1,x-phenylenebis(propane-3,1-diyl))bis(1-methylpyrrolidin-1-ium) compound.

Embodiment 12. A method of producing a 1,1'-(1,x-phenylenebis(propane-3,1-diyl))bis(1-methylpyrrolidin-1-ium) compound, where x is 2, 3 or 4, the method comprising:

reacting 1-(prop-2-yn-1-yl)pyrrolidine (which is optionally produced by reacting a 3-haloprop-1-yne with pyrrolidine) with a 1,x-dihalo-substituted benzene to produce a compound of formula (IVA), (IVB) or (IVC):

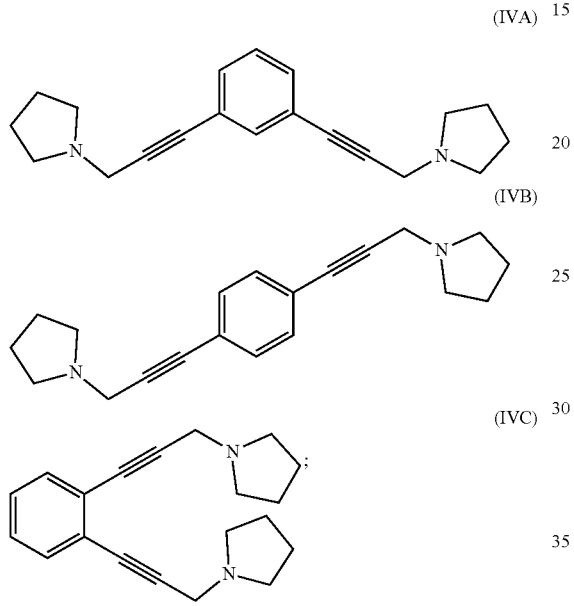

(IVA)

(IVB)

(IVC);

hydrogenating at least part of the compound of formula (IVA), (IVB) or (IVC) to produce a compound of formula (VA), (VB) or (VC):

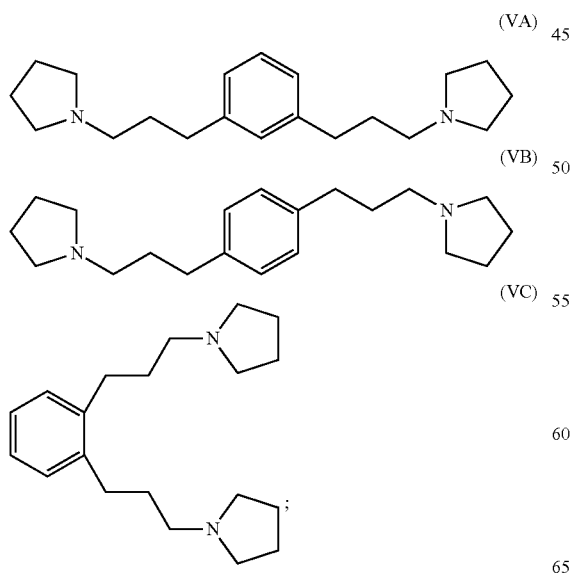

(VA)

(VB)

(VC);

and reacting at least part of the compound of formula (VA), (VB) or (VC) with a methyl halide to produce a 1,1'-(1,x-phenylenebis(propane-3,1-diyl))bis(1-methylpyrrolidin-1-ium) halide.

Embodiment 13. A method of producing a 1,1'-(1,x-phenylenebis(propane-3,1-diyl))bis(1-methylpyrrolidin-1-ium) compound, where x is 2, 3 or 4, the method comprising:

reacting a compound of formula (VI)

(VI)

where $R^1$ is a hydroxyl group or an alkyl- or aryl-sulfonate group, with a 1,x-dihalo-substituted benzene to produce a compound of formula (VIIA), (VIIB) or (VIIC):

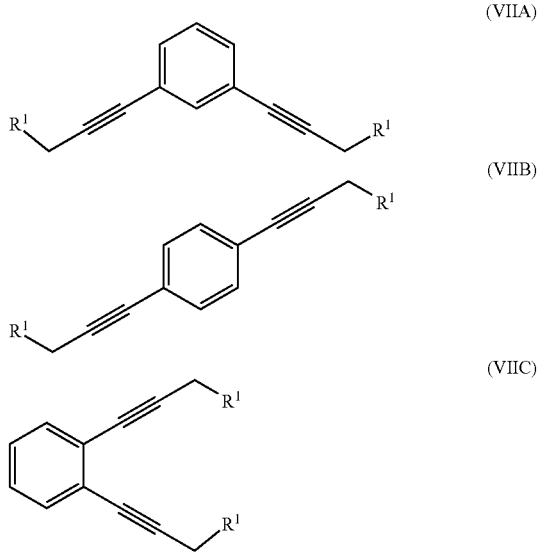

(VIIA)

(VIIB)

(VIIC)

wherein, when $R^1$ is an alkyl- or aryl-sulfonate group (e.g., 4-methylbenzenesulfonate), the method further comprises:

hydrogenating at least part of the compound of formula (VIIA), (VIIB) or (VIIC) to produce a compound of formula (VIIIA), (VIIIB) or (VIIIC):

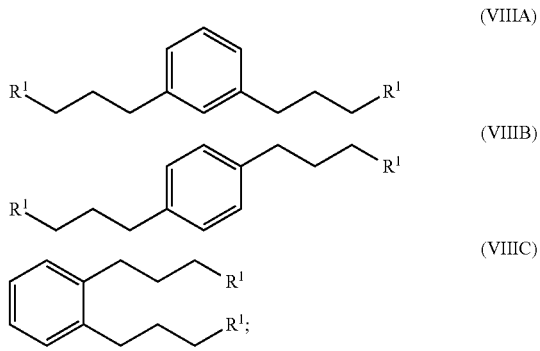

(VIIIA)

(VIIIB)

(VIIIC)

converting at least part of the compound of formula (VIIIA), (VIIIB) or (VIIIC) to a 1,1'-(1,x-phenylenebis(propane-3,1-diyl))bis(1-methylpyrrolidin-1-ium) compound by (i) reaction with 1-methylpyrrolidine or (ii) by reaction with pyrrolidine and then with a methyl halide;

optionally reacting at least part of the compound of formula (VIIA), (VIIB) or (VIIC) when $R^1$ is an alkyl- or aryl-sulfonate group with pyrrolidine to produce a compound of formula (IVA), (IVB) or (IVC):

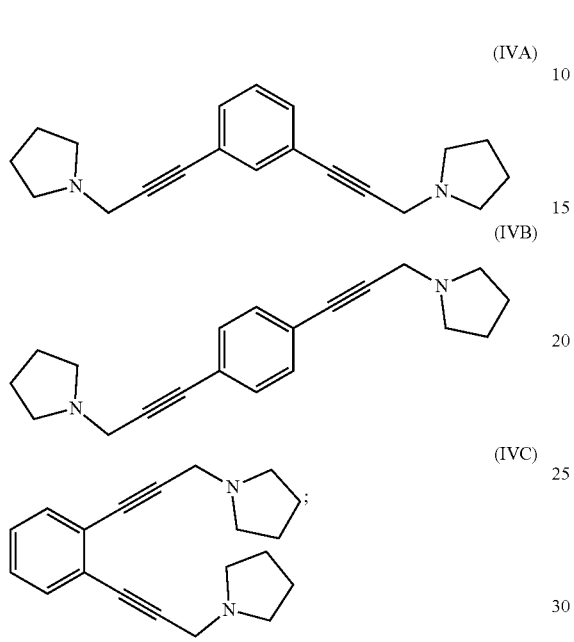

optionally hydrogenating at least part of the compound of formula (IVA), (IVB) or (IVC) to produce a compound of formula (VA), (VB) or (VC):

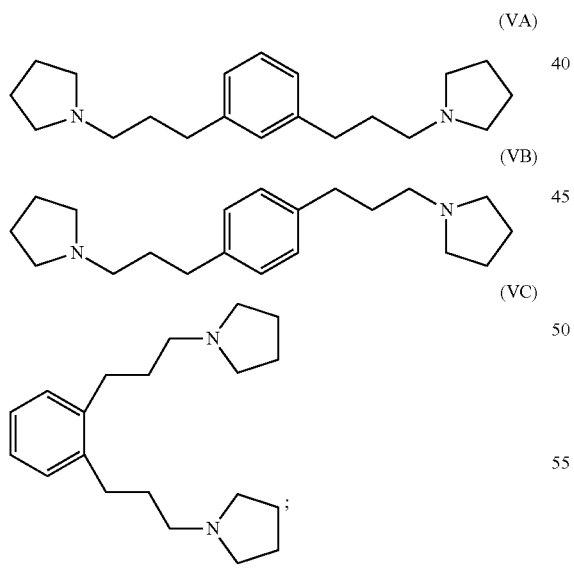

and optionally reacting at least part of the compound of formula (VA), (VB) or (VC) with a methyl halide to produce a 1,1'-(1,x-phenylenebis(propane-3,1-diyl))bis(1-methyl-pyrrolidin-1-ium) halide.

Embodiment 14. The method of embodiment 13, wherein $R^1$ is a hydroxyl group and the method further comprises:

reacting at least part of the compound of formula (VIIA), (VIIIB) or (VIIC) with an alkyl- or aryl-sulfonyl halide such as p-toluenesulfonyl chloride to produce a compound of formula (IXA), (IXB) or (IXC):

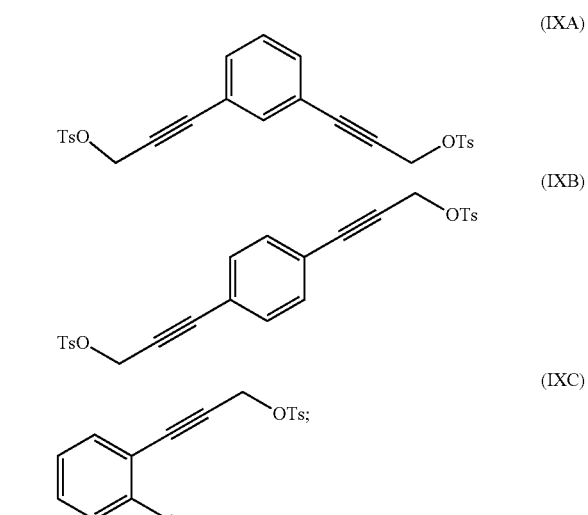

optionally hydrogenating at least part of the compound of formula (IXA), (IXB) or (IXC) to produce a compound of (XA), (XB) or (XC):

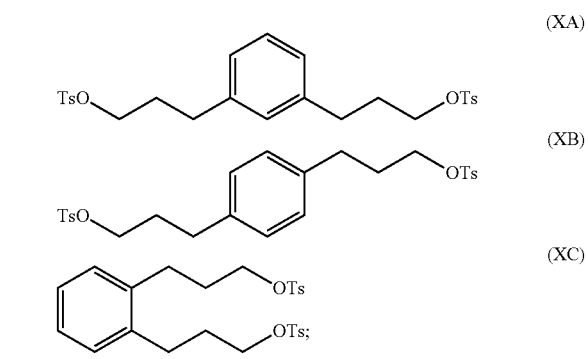

optionally converting at least part of the compound of formula (XA), (XB) or (XC) into a 3,3-(1,x-phenylene)bis(propane-3,1-diyl)bis(1-methylpyrrolidinium) compound by (i) reaction with 1-methylpyrrolidine or (ii) by reaction with pyrrolidine and then with a methyl halide;

optionally reacting at least part of the compound of formula (IXA), (IXB) or (IXC) with pyrrolidine to produce a compound of formula (IVA), (IVB) or (IVC):

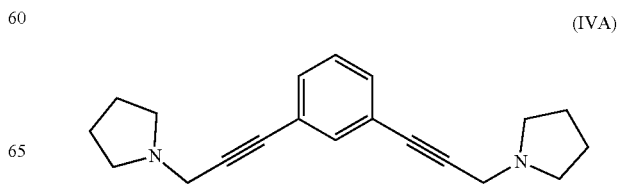

(IVB)

(IVC)

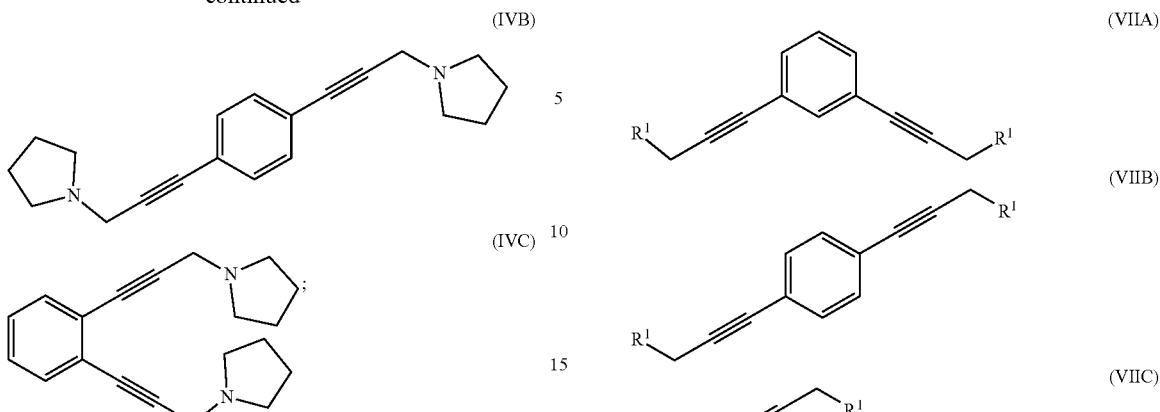

(VIIA)

(VIIB)

(VIIC)

optionally hydrogenating at least part of the compound of formula (IVA), (IVB) or (IVC) to produce a compound of formula (VA), (VB) or (VC):

hydrogenating at least part of the compound of formula (VIIA), (VIIB) or (VIIC) to produce a compound of formula (VIIIA), (VIIIB) or (VIIIC), respectively:

(VA)

(VB)

(VC)

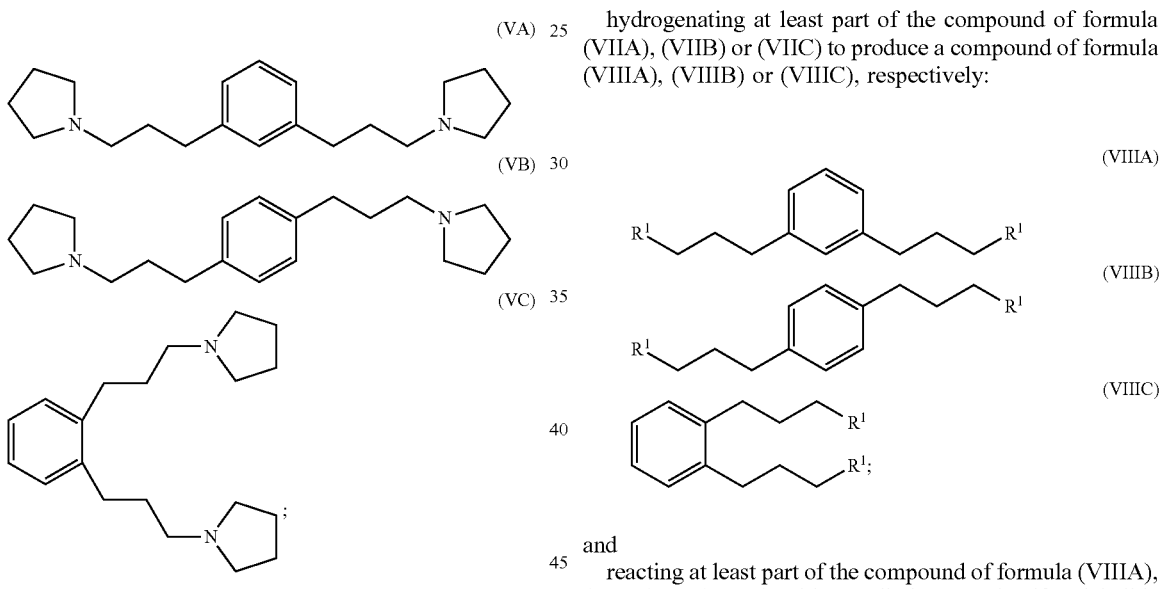

(VIIIA)

(VIIIB)

(VIIIC)

and optionally reacting at least part of the compound of formula (VA), (VB) or (VC) with a methyl halide to produce a 1,1'-(1,x-phenylenebis(propane-3,1-diyl))bis(1-methyl-pyrrolidin-1-ium) halide.

Embodiment 15. A method of producing a 1,1'-(1,x-phenylenebis(propane-3,1-diyl))bis(1-methylpyrrolidin-1-ium) compound, where x is 2, 3 or 4, the method comprising:

reacting a compound of formula (VI)

and reacting at least part of the compound of formula (VIIIA), (VIIIB) or (VIIIC) with an alkyl- or aryl-sulfonyl halide such as p-toluenesulfonyl chloride to produce a compound of formula (XA), (XB) or XC, respectively:

(VI)

where $R^1$ is a hydroxyl group, with 1,x-dihalo-substituted benzene to produce a compound of formula (VIIA), (VIIB) or (VIIC):

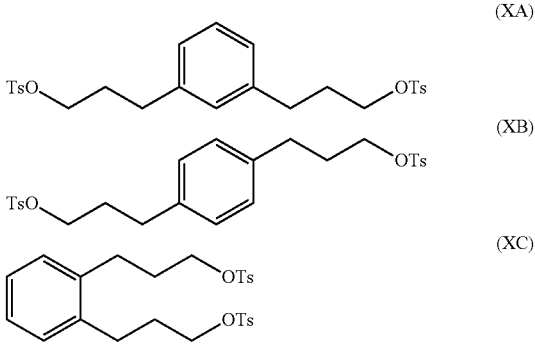

(XA)

(XB)

(XC)

converting at least part of the compound of formula (XA), (XB) or (XC) to a 1,1'-(1,x-phenylenebis(propane-3,1-diyl))

bis(1-methylpyrrolidin-1-ium) compound by (i) reaction with 1-methylpyrrolidine or (ii) by reaction with pyrrolidine and then with a methyl halide.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. An organic nitrogen compound comprising a dication of formula I, II and III:

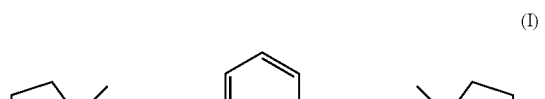
(I)

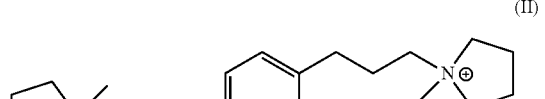
(II)

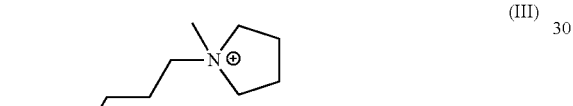
(III)

2. A method of producing a 1,1'-(1,x-phenylenebis(propane-3,1-diyl))bis(1-methylpyrrolidin-1-ium) compound, where x is 2, 3 or 4, the method comprising:
reacting 1,x-bis(halomethyl)benzene with a dialkyl malonate to produce a tetraalkyl 2,2'-(1,x-phenylenebis(methylene))dimalonate;
converting at least part of the tetraalkyl 2,2'-(1,x-phenylenebis(methylene))dimalonate to 3,3'-(1,x-phenylene)dipropanoic acid;
reducing at least part of the 3,3'-(1,x-phenylene)dipropanoic acid, or an ester thereof, to 3,3'-(1,x-phenylene)bis(propan-1-ol));
reacting at least part of the 3,3'-(1,x-phenylene)bis(propan-1-ol)) with an alkyl- or aryl-sulfonyl halide to produce the corresponding sulfonate diester;
reacting at least part of the sulfonate diester with pyrrolidine to produce 1,x-bis(3-(pyrrolidin-1-yl)propyl)benzene; and
reacting at least part of the 1,x-bis(3-(pyrrolidin-1-yl)propyl)benzene with a methyl halide to produce a 1,1'-(1,x-phenylenebis(propane-3,1-diyl))bis(1-methylpyrrolidin-1-ium) halide.

3. The method of claim 2 wherein at least part of the 3,3'-(1,x-phenylene)bis(propan-1-ol)) is reacted with p-toluenesulfonyl chloride.

4. A method of producing a 1,1'-(1,x-phenylenebis(propane-3,1-diyl))bis(1-methylpyrrolidin-1-ium) compound, where x is 2, 3 or 4, the method comprising:
reacting 1,x-bis(halomethyl)benzene with a dialkyl malonate to produce a tetraalkyl 2,2'-(1,x-phenylenebis(methylene))dimalonate;
converting at least part of the tetraalkyl 2,2'-(1,x-phenylenebis(methylene))dimalonate to 3,3'-(1,x-phenylene)dipropanoic acid;
reducing at least part of the 3,3'-(1,x-phenylene)dipropanoic acid, or an ester thereof, to 3,3'-(1,x-phenylene)bis(propan-1-ol));
reacting at least part of the 3,3'-(1,x-phenylene)bis(propan-1-ol)) with an alkyl- or aryl-sulfonyl halide to produce the corresponding sulfonate diester; and
reacting at least part of the sulfonate diester with 1-methylpyrrolidine to produce a 1,1'-(1,x-phenylenebis(propane-3,1-diyl))bis(1-methylpyrrolidin-1-ium) compound.

5. The method of claim 4 wherein at least part of the 3,3'-(1,x-phenylene)bis(propan-1-ol)) is reacted with p-toluenesulfonyl chloride.

6. A method of producing a 1,1'-(1,x-phenylenebis(propane-3,1-diyl))bis(1-methylpyrrolidin-1-ium) compound, where x is 2, 3 or 4, the method comprising:
reacting 1-(prop-2-yn-1-yl)pyrrolidine with a 1,x-dihalo-substituted benzene to produce a compound of formula (IVA), (IVB) or (IVC):

(IVA)

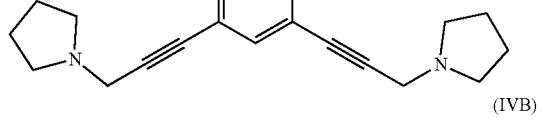
(IVB)

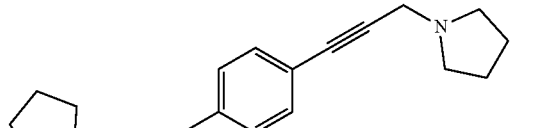
(IVC)

hydrogenating at least part of the compound of formula (IVA), (IVB) or (IVC) to produce a compound of formula (VA), (VB) or (VC):

(VA)

-continued

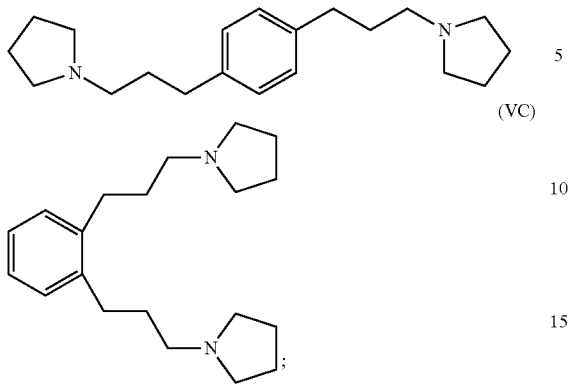

and reacting at least part of the compound of formula (VA), (VB) or (VC) with a methyl halide to produce a 1,1'-(1,x-phenylenebis(propane-3,1-diyl))bis(1-methylpyrrolidin-1-ium) halide.

7. The method of claim 6, wherein the 1-(prop-2-yn-1-yl)pyrrolidine is produced by reacting a 3-haloprop-1-yne with pyrrolidine.

8. A method of producing a 1,1'-(1,x-phenylenebis(propane-3,1-diyl))bis(1-methylpyrrolidin-1-ium) compound, where x is 2, 3 or 4, the method comprising:

reacting a compound of formula (VI)

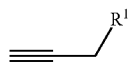     (VI)

where $R^1$ is a hydroxyl group or an alkyl- or aryl-sulfonate group, with a 1,x-dihalo-substituted benzene to produce a compound of formula (VIIA), (VIIB) or (VIIC):

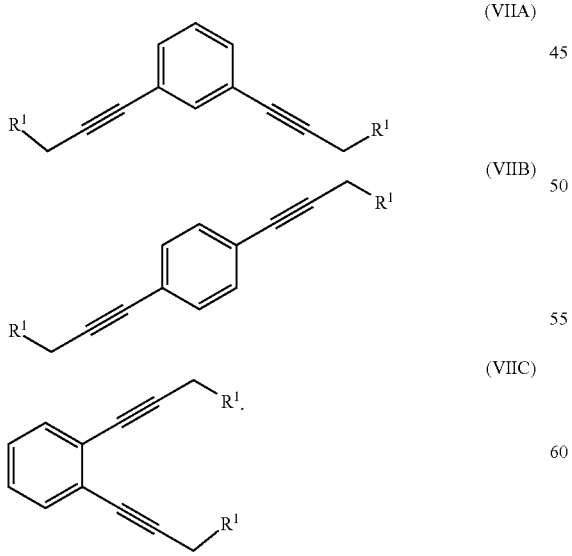

9. The method of claim 8, wherein $R^1$ is an alkyl- or aryl-sulfonate group and the method further comprises:

hydrogenating at least part of the compound of formula (VIIA), (VIIB) or (VIIC) to produce a compound of formula (VIIIA), (VIIIB) or (VIIIC):

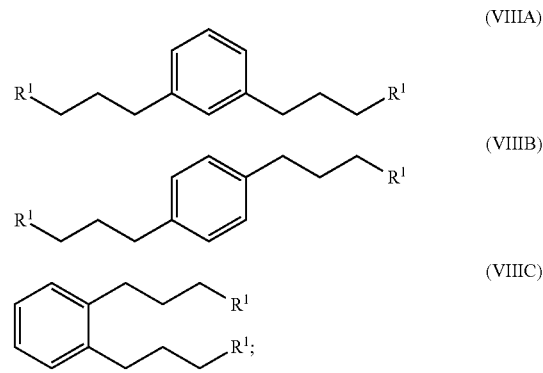

and converting at least part of the compound of formula (VIIIA), (VIIIB) or (VIIIC) to a 1,1'-(1,x-phenylenebis(propane-3,1-diyl))bis(1-methylpyrrolidin-1-ium) compound by (i) reaction with 1-methylpyrrolidine or (ii) by reaction with pyrrolidine and then with a methyl halide.

10. The method of claim 9, wherein $R^1$ is a 4-methylbenzenesulfonate group.

11. The method of claim 8, wherein $R^1$ is an alkyl- or aryl-sulfonate group and the method further comprises:

reacting at least part of the compound of formula (VIIA), (VIIB) or (VIIC) with pyrrolidine to produce a compound of formula (IVA), (IVB) or (IVC):

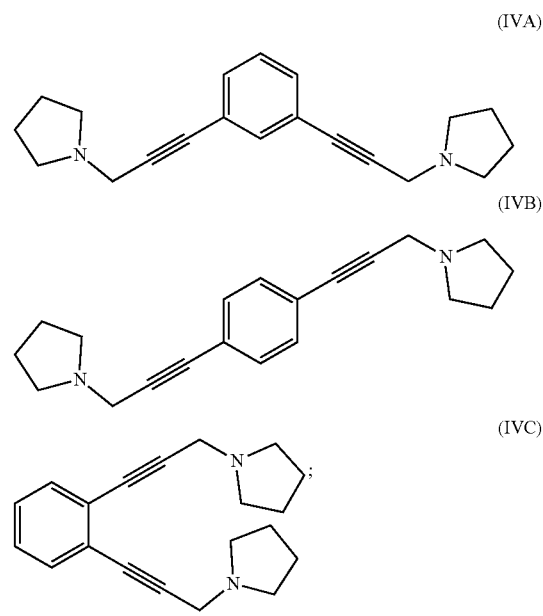

hydrogenating at least part of the compound of formula (IVA), (IVB) or (IVC) to produce a compound of formula (VA), (VB) or (VC):

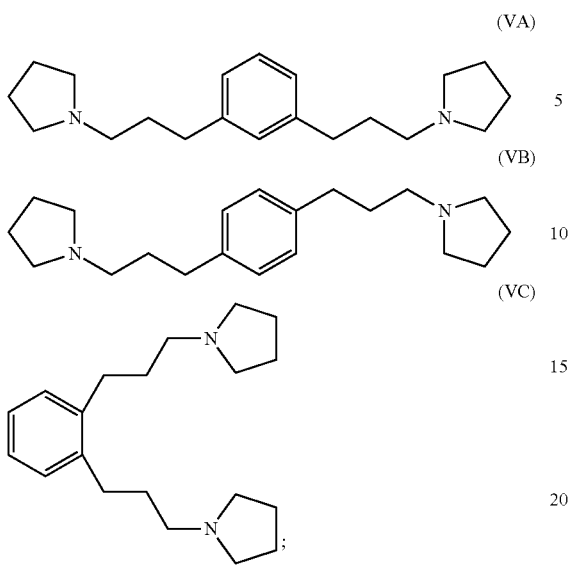

and reacting at least part of the compound of formula (VA), (VB) or (VC) with a methyl halide to produce a 1,1'-(1,x-phenylenebis(propane-3,1-diyl))bis(1-methylpyrrolidin-1-ium) halide.

12. The method of claim 11, wherein $R^1$ is a 4-methylbenzenesulfonate group.

13. The method of claim 8, wherein $R^1$ is a hydroxyl group and the method further comprises:

reacting at least part of the compound of formula (VIIA), (VIIIB) or (VIIC) with an alkyl- or aryl-sulfonyl halide such as p-toluenesulfonyl chloride to produce a compound of formula (IXA), (IXB) or (IXC):

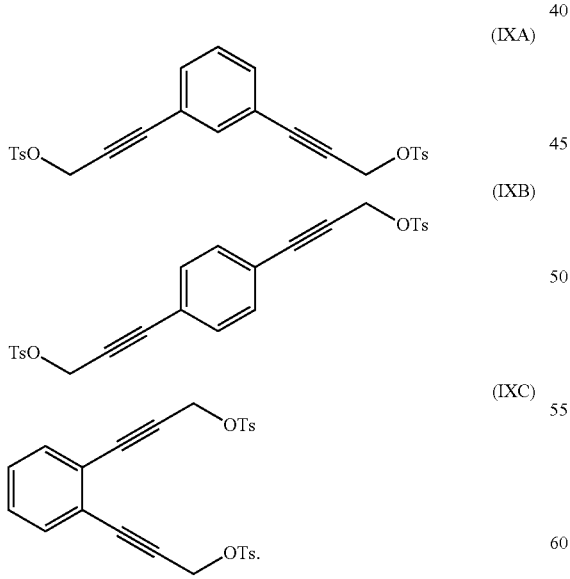

14. The method of claim 13 and further comprising:

hydrogenating at least part of the compound of formula (IXA), (IXB) or (IXC) to produce a compound of (XA), (XB) or (XC):

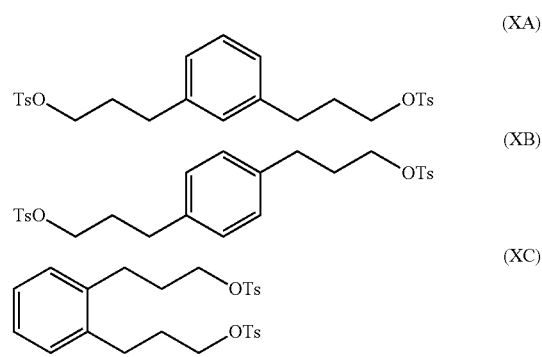

(i4) converting at least part of the compound of formula (XA), (XB) or (XC) into a 3,3-(1,x-phenylene)bis(propane-3,1-diyl)bis(1-methylpyrrolidinium) compound by (i) reaction with 1-methylpyrrolidine or (ii) by reaction with pyrrolidine and then with a methyl halide.

15. The method of claim 13 and further comprising:

reacting at least part of the compound of formula (IXA), (IXB) or (IXC) with pyrrolidine to produce a compound of formula (IVA), (IVB) or (IVC):

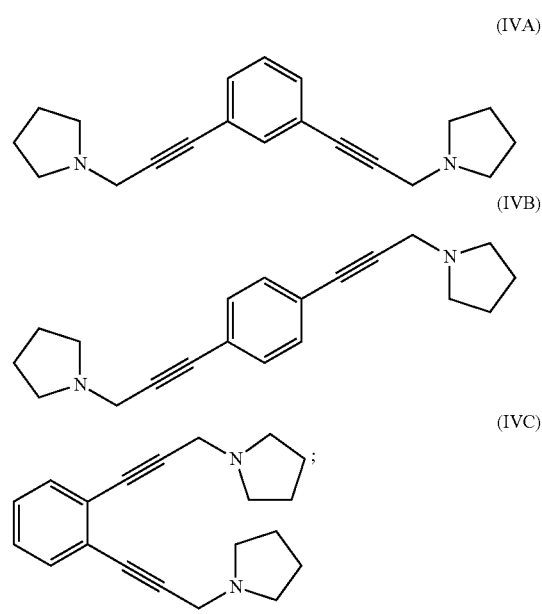

hydrogenating at least part of the compound of formula (IVA), (IVB) or (IVC) to produce a compound of formula (VA), (VB) or (VC):

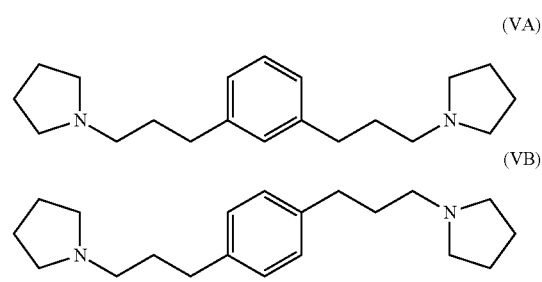

hydrogenating at least part of the compound of formula (VIIA), (VIIB) or (VIIC) to produce a compound of formula (VIIIA), (VIIIB) or (VIIIC), respectively:

(VC)
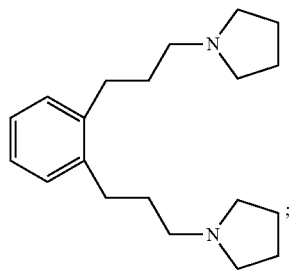

(VIIIA)
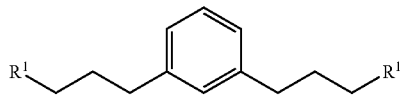

(VIIIB)
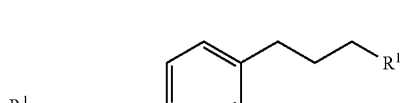

(VIIIC)
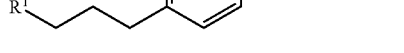

and reacting at least part of the compound of formula (VA), (VB) or (VC) with a methyl halide to produce a 1,1'-(1,x-phenylenebis(propane-3,1-diyl))bis(1-methylpyrrolidin-1-ium) halide.

16. A method of producing a 1,1'-(1,x-phenylenebis(propane-3,1-diyl))bis(1-methylpyrrolidin-1-ium) compound, where x is 2, 3 or 4, the method comprising:

reacting a compound of formula (VI)

(VI)

where $R_1$ is a hydroxyl group, with 1,x-dihalo-substituted benzene to produce a compound of formula (VIIA), (VIIB) or (VIIC):

(VIIA)
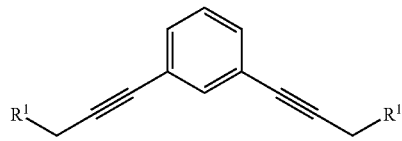

(VIIB)
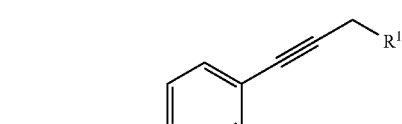

(VIIC)
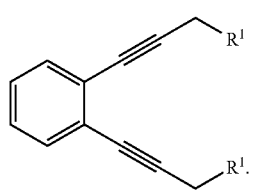

and reacting at least part of the compound of formula (VIIIA), (VIIIB) or (VIIIC) with an alkyl- or aryl-sulfonyl halide such as p-toluenesulfonyl chloride to produce a compound of formula (XA), (XB) or XC, respectively:

(XA)
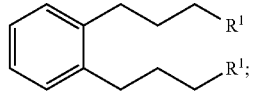

(XB)
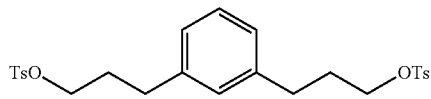

(XC)
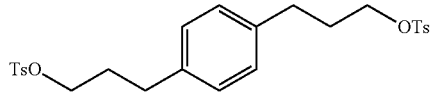

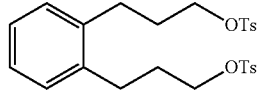

converting at least part of the compound of formula (XA), (XB) or (XC) to a 1,1'-(1,x-phenylenebis(propane-3,1-diyl))bis(1-methylpyrrolidin-1-ium) compound by (i) reaction with 1-methylpyrrolidine or (ii) by reaction with pyrrolidine and then with a methyl halide.

\* \* \* \* \*